(12) United States Patent
Von Dreele

(10) Patent No.: US 7,469,036 B2
(45) Date of Patent: Dec. 23, 2008

(54) ANALYSIS OF MACROMOLECULES, LIGANDS AND MACROMOLECULE-LIGAND COMPLEXES

(75) Inventor: Robert B. Von Dreele, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 611 days.

(21) Appl. No.: 10/159,958

(22) Filed: May 31, 2002

(65) Prior Publication Data

US 2003/0198997 A1 Oct. 23, 2003

Related U.S. Application Data

(60) Provisional application No. 60/374,015, filed on Apr. 19, 2002.

(51) Int. Cl.
*G01N 23/207* (2006.01)
(52) U.S. Cl. ............................. 378/75; 506/9; 702/27
(58) Field of Classification Search ............... None
See application file for complete search history.

(56) References Cited

U.S. PATENT DOCUMENTS 5,571,902 A 11/1996 Ravikumar et al.
5,891,643 A 4/1999 Fesik et al.
6,297,021 B1 * 10/2001 Nienaber et al. ............ 435/7.1

OTHER PUBLICATIONS

Von Dreele, R. B. "Binding of N-acetylglucosamine to chicken egg lysozyme: a powder diffraction study" Acta Cryst. 2001, D57, 1836-1842.*
Von Dreele, et al. "The first protein crystal structure determined from high-resolution X-ray powder diffraction data: a variant of T3R3 human insulin-zinc complex produced by grinding" Acta Cryst. 2000, 1549-1553.*
Vaguine, A. A.; Richelle, J.; Wodak, S. J. "SFCHECK: a unified set of procedures for evaluating the quality of macromolecular structure-factor data and their agreement with the atomic model" Act Cryst. 1999, D55, 191-205.*
Kumazawa, S.; Kubota, Y.; Takata, M.; Sakata, M. "MEED: a program package for electron-density-distribution calculation by the maximum-entropy method" J. Appl. Cryst. 1993, 26, 453-457.*
Von Dreele, "Combined Rietveld and stereochemical restraint refinement of a protein crystal structure" J. Appl. Cryst. 1999, 32, 1084-1089.*

Lengauer, T.; Rarey, M. "Computation methods for biomolecular docking" Curr. Opin. Structur. Biol. 1996, 6, 402-406.*
Engel et al. "PowderSolve—a complete package for crystal structure solution from the powder diffraction patterns" J. Appl. Cryst. 1999, 32, 1169-1179.*
Attwood, T. K.; Miller, C. J. "Which craft is best in bioinformatics" Computers and Chemistry 2001, 25, 329-339.*
Von Dreele, R.B. et al.; "The First Protein Crystal Structure Determined From High Resolution X-Ray Powder Diffraction Data: A Variant of of T3R3 Human Insulin-Zinc Complex Produced by Grinding," Acta Crystallographica Section D. vol. D56, pp. 1549-1553, (2000).
Oldfield, T.J.; "X-Ligand: An Application for the Automated Addition of Flexible Ligands into Electron Density," Acta Crystallographica Section D. vol. D57, pp. 696 thru 705, (2001).
Chayen, Naomi F..; "Recent Advances in Methodology for the Crystallization of Biological Macromolecules," Journal of Crystal Growth, vol. 198/199, pp. 649 thru 655, (1999).
Amos, Linda A. et al.; "Arrangement of Protofilaments in Two Forms of Tubulin Crystal Induced by Yinblastine," Journal of Molecular Biology, vol. 178, pp. 711 thru 729, (1984).
Richards, Jane P. et al.; "Preparation of a Microcrystalline Suspension Formulation of Lys (B28) Pro (B29)- Human Insulin with Ultralente Properties," Journal of Pharmaceutical Sciences, vol. 88, No. 9, pp. 861 thru 867, Sep. 1999.
Driessen. H. et al.; "Restrain: Restrained Structure-Factor Least-Squares Refinement Program for Macromolecular Structures," Journal of Applied Crystallography, vol. 22, pp. 510-516, (1989).
Laskowski, Roman A. et al.; "Procheck: A Program to Check the Stereochemical Quality of Protein Structures," Journal of Applied Crystallography, vol. 26, pp. 283-291, (1993).
McCusker, L.B. et al.; "Rietveld Refinement Guidelines," Journal of Applied Crystallography, vol. 32, pp. 36-50, (1999).

(Continued)

*Primary Examiner*—Jon D Epperson
(74) *Attorney, Agent, or Firm*—John P. O'Banion

(57) ABSTRACT

A method for determining atomic level structures of macromolecule-ligand complexes through high-resolution powder diffraction analysis and a method for providing suitable microcrystalline powder for diffraction analysis are provided. In one embodiment, powder diffraction data is collected from samples of polycrystalline macromolecule and macromolecule-ligand complex and the refined structure of the macromolecule is used as an approximate model for a combined Rietveld and stereochemical restraint refinement of the macromolecule-ligand complex. A difference Fourier map is calculated and the ligand position and points of interaction between the atoms of the macromolecule and the atoms of the ligand can be deduced and visualized. A suitable polycrystalline sample of macromolecule-ligand complex can be produced by physically agitating a mixture of lyophilized macromolecule, ligand and a solvent.

4 Claims, 9 Drawing Sheets

OTHER PUBLICATIONS

Engel, G.E. et al.; "Powdersolve—A Complete Package for Crystal Structure Solution From Powder Diffraction Patterns," Journal of Applied Crystallography, vol. 32, pp. 1169-1179, (1999).

Weber, Patricia C.; "Methods in Enzymology—vol. 276" 'Overview of Protein Crystallization Methods.' pp. 13 thru 22, Academic Press, (1997).

Brunger, Axel T.; "Methods in Enzymology—vol. 276." 'Patterson Correlation Searches and Refinement.' pp. 558 thru 580, Academic Press, (1997).

Korszun, Z. Richard; "Methods in Enzymology—vol. 276." 'Neutron Macromolecular Crystallography.' pp. 218 thru 232. Academic Press (1997).

Mattos, Carla and Ringe, Dagmar; "Locating and Characterizing Binding Sites on Proteins," Nature Biotechnology, vol. 14, pp. 595 thru 599, May 1996.

Mattos, Carla and Ringe, Dagmar; "Proteins in Organic Solvents," Current Opinion in Structural Biology, vol. 11, pp. 761-764, (2001).

Teplyakov, Alexei et al.; "On the Choice of an Optimal Wavelength in Macromolecular Crystallography," Acta Crystallography, vol. D54, pp. 610-614, (1998).

Lugovskoy, Alexey A. et al.; "A Novel Approach for Characterizing Protein Liquid Complexes: Molecular Basis for Specificity of Small-Molecule Bcl-2 Inhibitors," Journal of American Chemical Society, vol. 124, No. 7, pp. 1234 thru 1240, (2002).

Ota, Nobuyuki and Agard, David A.; "Binding Mode Prediction for a Flexible Ligand in a Flexible Pocket Using Multi-Conformation Simulate Annealing Pseudo Crystallographic Refinement," Journal of Miolecular Biology, vol. 314, pp. 607-617, (2001).

Berman, Helen M. et al.; "The Protein Data Bank," Nucleic Acids Research, vol. 28, No. 1, pp. 235-242, (2000).

Chayen, Naomi E.; "Recent Advances in Methodology for the Crystallization of Biological Macromolecules," Journal of Crystal Growth, vol. 198/199, pp. 649-655, (1999).

Chu, Yeh-Ho et al.; "Affinity Capillary Electrophoresis—Mass Spectrometry for Screening Combinatorial Libraries," Journal of Chemical Society, vol. 118, pp. 7827-7835 (1996).

Ecker, David J. et al.; "Combinatorial Drug Discovery: Which Methods Will Produce the Greatest Value?" BioTechnology, vol. 13, pp. 351-360, Apr. 1995.

Guex, Nicolas et al.; "Swiss-Model and the Swiss-Pdbviewer: An Environment for Comparative Protein Modeling," Electrophoresis, vol. 18, pp. 2714-2723, (1997).

Karlsson, Robert et al.; "Kinetic Analysis of Monoclonal Antibody-Antigen Interactions with a New Biosensor Based Analytical System," Journal of Immunological Methods, vol. 145, pp. 229-240 (1991).

Kumazawa, Shintaro et al.; "Meed: A Program Package for Electron-Density-Distribution Calculation by the Maximum-Entropy Method," Journal of Applied Crystallography, vol. 26, pp. 453-457 (1993).

Moult, John et al.; "Critical Assessment of Methods of Protein Structure Predictions (CASP): Round III," Proteins: Structure, Function, and Genetics Supplement, vol. 3, pp. 2-6 (1999).

Sim, G.A.; "A Note on the Heavy-Atom Method," Acta. Cryst., vol. 13, pp. 511-512 (1960.

Sternberg, Nat et al.; "Display of Peptides and Proteins on the Surface of Bacteriophase (Lambda)," Proc. Natl. Acad. Sci., vol. 92, pp. 1609-1613, Feb. 1995.

Udenfriend, Sidney et al.; "Scintillation Proximity Assay: A Sensitive and Continuous Isotopic Method for Monitoring Ligand/Receptor and Antigen/Antibody Interactions." Analytical Biochemistry, vol. 161, pp. 494-500 (1987).

Von Dreele, R.B.; "Combined Rietveld and Stereochemical Restraint Refinement of a Protein Crystal Structure," Journal of Applied Crystallography, vol. 32, pp. 1084-1089 (1999).

Bergfors, Terese M. ed.; "Protein Crystallization: Techniques, Strategies, and Tips." Cover page-Preface pp. v-vii, Chapter One (Alexander McPherson) pp. 1-6, International University Line. La Jolla, CA (1999).

Berson, Solomon A. et al.; "General Principles of Radioimmunoassay," Clinical Chimica Acta., vol. 22, pp. 51-69 (1968).

Brown, T.A.; "DNA Sequencing the Basics," Cover page, title page, pp. 1-6, IR1, Press, Oxford University Press, New York (1994).

Cheetham, Anthony K.; "Abinitio Structure Solution with Powder Diffraction Data," Chapeter 15, pp. 276-292, from 'The Rietveld Method,' R.A. Young, ed.; International Union of Crystallography, Oxford University Press (1993).

Copeland, Robert A.; "Methods for Protein Analysis," Cover page, title page, pp. 1-16, Chapman & Hall, New York (1994).

Karplus, Martin et al.; from Creighton, Thomas E. ed.; "Protein Folding," Cover page, title page, Chapter Four, pp. 127-195, W.H. Freeman Company, New York (1992).

Drenth, Jan; "Principles of Protein X-Ray Crystallography," cover page, title page, Chapter 2, pp. 22-47, Springer Advanced Texts in Chemistry (1999).

Larson, Al & Von Dreele, R.B.; "General Structure Analysis System (GSAS)," Los Alamos National Laboratory Report LAUR 86-748, Cover page, pp. i-v, pp. 1-224 (2001).

Jenkins, Ron et al.; "Chemical Analysis: vol. 138: Introduction to X-Ray Powder Diffractometry," Winefordner, J.D. ed., Cover page, title page, pp. 231-259, John Wiley & Sons, Inc., New York (1996).

Wilson, Kenneth J. et al.; "Protein and Peptide Purification," Chapter 1 from Protein Sequencing, A Practical Approach, Findlay, J.B.C. et al. eds. Cover page, title page, pp. 1-41, Oxford University Press, New York (1989).

Palmer, R.A., "X-Ray Crystallographic Studies of Protein-Ligand Interactions," Chapter 1, pp. 1-98, from Protein-Ligand Interactions: Structure and Spectroscopy, Harding, S.E. et al. eds. Oxford University Press, New York (2001).

Kroemer, Romano T.; "Molecular Modeling," Chapter 2, pp. 99-121, from Protein-Ligand Interactions: Structure and Spectroscopy, Harding S.E. et al. eds. Oxford University Press, New York (2001).

Ramachandran, G.N. et al.; "Fourier Methods in Crystallography," Cover page, title page, pp. 1-33, John Wiley & Sons, Inc., New York (1970).

Smith, Bryan John ed.; "Protein Sequencing Protocols," Cover page, title page, pp. 17-24, Humana Press, Totowa, New Jersey (1997).

Czarnik, Anthony W.; Guest Editorial: "Accounts of Chemical Research," vol. 29, No. 3, Cover pae, pp. 112-113 (1996).

Hsieh-Wilson, Linda C. et al.; "Lessons From the Immune System: From Catalysis to Materials Science," Accounts of Chemical Research, vol. 29, No. 3, pp. 164-170 (1996).

DeWitt, Sheila Hobbs, et al.; "Combinatorial Organic Systhesis Using Parke-Davis' Diversomer Method," Accounts of Chemical Research, vol. 29, No. 3, pp. 114-122 (1996).

Armstrong, Robert W. et al.; "Multiple-Component Condensation Strategies for Combinatorial Library Synthesis," Accounts of Chemical Research, vol. 29, No. 3, pp. 123-131 (1996).

Ellman, Jonathan A.; "Design, Synthesis and Evaluation of Small-Molecule Libraries," Accounts of Chemical Research, vol. 29, No. 3, pp. 132-143 (1996).

Gordon, E.M. et al.; "Strategy and Tactics in Combinatorial Organic Synthesis: Applications to Drug Discovery," Accounts of Chemical Research, vol. 29, No. 3, pp. 144-154 (1996).

Still, W. Clark; "Discovery of Sequence-Selective Peptide Binding by Synthetic Receptors Using Encoded Combinatorial Libraries," Accounts of Chemical Research, vol. 29, No. 3, pp. 155-163 (1996).

Toraya, Hideo; "Position-Constrained and Unconstrained Powder-Pattern-Decomposition Methods," from 'The Rietveld Method.' Chapter 12, pp. 255-275, International Union of Crystallography, Oxford University Press (1993).

Von Dreele, R.B.; "Neutron Powder Diffraction," from 'Modern Powder Diffraction, Reviews in Mineralogy,' vol. 20, Chapter 11, pp. 331-369 (1989).

Erikson, John W. et al.; "Macromolecular X-Ray Crystallography and NMR as Tools for Structure-Based Drug Design," Annual Reports in Medicinal Chemistry, vol. 27, pp. 271-289 (1992).

Jefson, Martin R.; "Applications of NMR Spectroscopy to Protein Structure Determination," Annual Reports in Medicianl Chemistry, vol. 23, pp. 275-283 (1988).

Jonsson, U. et al.; "Real-Time Biospecific Interaction Analysis Using Surface Plasmon Resonance and a Sensor Chip Technology," Biotechniques, vol. 11, pp. 620-627 (1991).

Chen, E.Y.; "The Efficiency of Automated DNA Sequencing," Automated DNA Sequencing and Analysis, eds, Adams, Mark D. et al., Cover Page; Frontipiece, pp. 3 thru 10, Academic Press, San Diego, (1991).

Von Dreele, R.B.; "Protein-Drug Interaction," Modern Drug Discovery, vol. 4, No. 5, pp. 83-84, May 2001.

Von Dreele, R.B.; Combined Rietveld- and Stereochemical-Restrint Refinement with High-Resolution Powder Diffraction Data Offers a New Approach for Obtaining Protein Drug Structures, http://lansce.lanl.gov/research/pdf/Reitveld.pdf, pp. 1 & 2.

Balbirnie, Melinda et al.; "An Amyloid-Forming Peptide From the Yeast Prion Sup35 Reveals a Dehydrated B-Sheet Structure for Amyloid," Proc. Nat. Acad. Sci., vol. 98, No. 5, pp. 2375-2380, Feb. 27, 2001.

Bernal, J.D. et al.; "X-Ray and Crystallographic Studies of Plant Virus Preparations. III," Journal of General Physiology, vol. 25, pp. 147 thru 165 (1941).

van Gunsteren, W.F. et al.; "Biomolecular Simulation: The Gromos96 Manual and User Guide," Verlag der Fachvereine, Zurich, cover page + frontipiece + preface + introduction II-1 thru II-123 (1996).

Jonsson, U, et al.; "Real-Time Biospecific Interaction Analysis Using Surface Plasmon Resonance and a Sensor Chip Technology," Biotechniques, vol. 11, pp. 620-627 (1991).

Chen, E.Y.; "The Efficiency of Automated DNA Sequencing," Automated DNA Sequencing and Analysis, eds, Adams, Mark D. et al., Cover Page; Frontipiece, pp. 3 thru 10, Academic Press, San Diego, (1991).

Von Dreele, R.B.; "Protein-Drug Interaction," Modern Drug Discovery, vol. 4, No. 5, pp. 83-84, May 2001.

Balbirnie, Melinda et al.; "An Amyloid-Forming Peptide from the Yeast Prion SUP35 Reveals a Dehydrated B-Sheet Structure for Amyloid," Proc. Nat. Acad. Sci., vol. 98, No. 5, pp. 2375-2380, Feb. 27, 2001.

Bernal, J.D. et al.; "X-Ray and Crystallographic Studies of Plant Virus Preparations. III," Journal of General Physiology, vol. 25, pp. 147 thru 165 (1941).

van Gunsteren, W.F. et al.; "Biomolecular Simulation: The Gromos96 Manual and User Guide," Verlag der Fachvereine, Zurich, cover page + frontipiece + preface + introduction II-1 thru II-123 (1996).

* cited by examiner

ANALYSIS OF MACROMOLECULES, LIGANDS AND MACROMOLECULE-LIGAND COMPLEXES

CROSS-REFERENCE TO RELATED APPLICATIONS

This application claims priority from U.S. provisional application Ser. No. 60/374,015 filed on Apr. 19, 2002, incorporated by reference herein.

STATEMENT REGARDING FEDERALLY SPONSORED RESEARCH OR DEVELOPMENT

This invention was made with government support under Contract No. W-7405-ENG-36 awarded by the U.S. Department of Energy. The government may have certain rights in the invention.

REFERENCE TO A COMPUTER PROGRAM APPENDIX

Not Applicable

BACKGROUND OF THE INVENTION

1. Field of the Invention

This invention pertains generally to methods for elucidating the three-dimensional structure of complex molecules, and more particularly to methods for determining, evaluating and analyzing the secondary and tertiary structure of macromolecule-ligand complexes and binding mechanisms through powder diffraction.

2. Description of the Background Art

Recent drug design efforts have been greatly influenced by the idea that drugs or peptides may target macromolecules with specific receptors to affect their biological activity. Genomic sequencing and other developments in molecular biology in the last decade have identified greater numbers of enzymes, receptors, signaling proteins, hormones, oligonucleotides and the like that may be the target of molecular therapies. Understanding the relationship between the structure and function of various molecules is fundamental to the study of biological and other chemistry-based systems. Structure-function relationships are also important in understanding the function of enzymes, cellular communication, cellular control and feedback mechanisms, and pharmaceutical agents.

Certain macromolecules in nature are known to interact with other molecules having a specific 3-dimensional spatial and electronic distribution. Any macromolecule having such specificity may be generally referred to as a receptor, whether the macromolecule is an enzyme, a protein, a glycoprotein, an antibody, or an oligonucleotide sequence of DNA, RNA, or the like. The various molecules that associate with such receptors are referred to as ligands.

Various prior art procedures have been used in an effort to identify and characterize ligands that bind to receptors. Such procedures typically involve methods of searching and evaluating the nature of novel agents such as pharmacological or therapeutic agents (i.e., drug discovery) that are useful in human or animal health care or management, agriculturally useful chemicals, selective biocides for insects, weeds, or other pests, and catalytic and other entities that may be useful in industrial processes. Thus, it is understood in many fields, including the drug discovery field, the details of how a ligand, for example, a small molecule such as a drug molecule, interacts with a macromolecule, such as a protein, are at the heart of commercial use of such ligands. For example, the vast majority of small molecule drugs act by binding to a more or less specific site in one or more protein targets. The inhibitory or promotional efficacy of the drug is related to the manner in which the molecule interacts with the target site and accurate information on the details of this interaction at the atomic and molecular level is highly desired. If such data are available, it may be possible to identify modifications to the ligand (or, in some cases, to the protein) that will serve to improve properties such as efficacy, side effects, or the cost of manufacture of the drug.

Traditionally, drug discovery and optimization have involved the expensive and time-consuming process of synthesis and evaluation of single compounds bearing incremental structural changes. Further, such compounds were often carefully chemically analyzed and characterized prior to in vitro evaluation. These methods typically included evaluation of candidate ligand compounds for binding affinity to their target macromolecules, competition for the ligand binding site, or efficacy at the target as determined via inhibition, cell proliferation, activation or antagonism end points.

The process of drug discovery in particular has changed, in part, because of the progress and evolution of a number of technologies that impact this process. Drug discovery has evolved from what was, several decades ago, essentially random screening of natural or other products, into a scientific process that not only includes the rational and combinatorial design of large numbers of synthetic molecules as potential bioactive agents, such as agonists, antagonists, and inhibitors, but also includes the identification, and mechanistic and structural characterization of their biological targets, which may be, for example, polypeptides, proteins, or nucleic acids. These key areas of drug design and structural biology are of tremendous importance to the understanding and treatment of disease. However, significant hurdles still need to be overcome when trying to identify or design high affinity ligands for a particular biological target molecule. These hurdles include the difficulty of the task of elucidating the structure of targets and targets to which other molecules may be bound or associated; the large numbers of compounds that need to be generated in order to identify and evaluate new leads or to optimize existing leads; the need to dissect structural similarities and dissimilarities between these large numbers of compounds; correlating structural features to activity and binding affinity, and the fact that small structural changes can lead to large effects on the biological activities of compounds.

One way in which the drug discovery process has been accelerated is by the generation of large collections, libraries, or arrays of compounds. The strategy of discovery has moved from the selection of drug leads from among compounds that are individually synthesized and tested to the screening of large collections of compounds. These collections may be from natural sources (Stemberg et al., *Proc. Natl. Acad. Sci. USA*, 1995, 92, 1609-1613) or generated by synthetic methods such as combinatorial chemistry (Ecker and Crooke, *BioTechnology*, 1995, 13, 351-360 and U.S. Pat. No. 5,571,902). These collections of compounds may be generated as libraries of individual, well-characterized compounds that may be synthesized, via high throughput, parallel synthesis or as a mixture or a pool of up to several hundred or even several thousand molecules synthesized by split-mix or other combinatorial methods.

Screening of such combinatorial libraries has usually involved a binding assay to determine the extent of ligand-receptor interaction (Chu et al., *J. Am. Chem. Soc.*, 1996, 118, 7827-35). Often the ligand or the target receptor is immobilized onto a surface such as a polymer bead or plate. The identity of the ligand or ligands that bind to the receptor is known if individual characterized ligands have been applied at different spatial positions. In the case where mixtures of ligands or uncharacterized ligands are used they may be released and identified following detection of a binding event. However, solid phase screening assays can be rendered difficult by non-specific interactions. Whether screening of combinatorial libraries is performed via solid-phase, solution methods or otherwise, it can be a challenge to identify those components of the library that bind to the target in a rapid and effective manner and which, hence, are of greatest interest. This is a process that needs to be improved to achieve ease and effectiveness in combinatorial and other drug discovery processes.

Several techniques have been used in the characterization of receptor-ligand interactions including enzyme-linked immunosorbent assay ELISA (Kemeny and Challacombe, in *ELISA and other Solid Phase Immunoassays: Theoretical and Practical Aspects*; Wiley, New York, 1988) and radioligand binding assays (Berson and Yalow, Clin. Chim. Acta, 1968, 22, 51-60; Chard, in *An Introduction to Radioimmunoassay and Related Techniques*, Elsevier, Amsterdam/New York, 1982), the use of surface-plasmon resonance (Karlsson, Michaelsson and Mattson, *J. Immunol. Methods*, 1991, 145, 229; Jonsson et al., *Biotechniques*, 1991, 11, 620), and scintillation proximity assays (Udenfriend, Gerber and Nelson, *Anal. Biochem.*, 1987, 161, 494-500). Radioligand binding assays are typically useful only when assessing competition between the binding of an unknown at a binding site and a radioligand, and also require the use of radioactive materials. The surface-plasmon resonance technique is more straightforward to use, but is also quite costly. Conventional biochemical assays of binding kinetics, and dissociation and association constants are also helpful in elucidating the nature of the target-ligand interactions. These approaches are generally helpful in the detection of receptor-ligand binding events but do not yield detailed structural information.

Several approaches to facilitating the understanding of the structure of therapeutic targets have also been developed so as to accelerate the process of drug discovery and development. These include developments in the sequencing of proteins and nucleic acids (Smith, in *Protein Sequencing Protocols*, Humana Press, Totowa, N.J., 1997; Findlay and Geisow, in *Protein Sequencing: A Practical Approach*, IRL Press, Oxford, 1989; Brown, in *DNA Sequencing*, IRL Oxford University Press, Oxford, 1994; Adams, Fields and Venter, in *Automated DNA Sequencing and Analysis*, Academic Press, San Diego, 1994). A drawback of present sequencing techniques, however, is their inability to reveal anything more than the primary structure, or sequence, of the target macromolecule.

Other techniques have been employed in an effort to elucidate secondary and tertiary structures of macromolecules, for example, Nuclear Magnetic Resonance (NMR) (Jefson, *Ann. Rep. in Med. Chem.*, 1988, 23, 275; Erikson and Fesik, *Ann. Rep. in Med. Chem.*, 1992, 27, 271-289), single crystal X-ray crystallography (Erikson and Fesik, *Ann. Rep. in Med. Chem.*, 1992, 27, 271-289) and the use of computer algorithms to attempt the prediction of protein folding (Copeland, in *Methods of Protein Analysis: A Practical Guide to Laboratory Protocols*, Chapman and Hall, New York, 1994; Creighton, in *Protein Folding*, W. H. Freeman and Co., 1992).

Likewise, advances have occurred in the chemical synthesis of compounds for high-throughput biological screening. In certain drug discovery efforts, collections of molecules or "libraries", natural or synthetic, are prepared and screened for molecules having a specified bioactivity, as indicated initially by detection of binding between one or more species or ligands in the library and a "target" molecule with which it binds to influence some biological process. More specifically, libraries consist of a complex assortment of molecules containing one or more ligands that may bind to a target of interest. The identification of ligands that bind may provide "hits" that have a desired biological activity, e.g., as a potential drug candidate. As methods have become available to screen these libraries more effectively, interest in exploiting "rational design" or the "directed molecular evolution" approach has increased. The construction and screening of small molecule libraries, including non-peptide libraries has also been reviewed. See, Special Issue on Combinatorial Libraries *Accounts of Chemical Sciences*, 29:111-170, 1996.

Combinatorial chemistry, computational chemistry, and the synthesis of large collections of mixtures of compounds or of individual compounds have all facilitated the rapid synthesis of large numbers of compounds for in vitro screening. Despite these advances, the process of drug discovery and optimization entails a sequence of difficult steps. This process can also be an expensive one because of the costs involved at each stage and the need to screen large numbers of individual compounds. Moreover, the structural features of target receptors can be elusive. Thus, current techniques and protocols for the study of combinatorial libraries against a variety of biologically relevant targets have many shortcomings. The tedious nature, high cost, multi-step character, and low sensitivity of many of the above-mentioned screening technologies are shortcomings of the currently available tools. Further, available techniques do not always afford the most relevant structural information. Also, the need for customized reagents and experiments for specific tasks is a challenge for the practice of current drug discovery and screening technologies.

As noted above, two of the most commonly applied methods for determining the structures of macromolecule-ligand complexes involve either gathering and interpreting high-resolution solution NMR spectra, or gathering and analyzing single crystal diffraction spectra on the complex.

Solution NMR is performed on an aqueous solution of macromolecules, while the molecules tumble and vibrate with thermal motion. NMR detects chemical shifts of atomic nuclei with nonzero spin. The shifts depend on the electronic environments of the nuclei, namely, the identities and distances of nearby atoms. $^1$H is the only atom occurring in sufficient abundance in natural macromolecules to be usefully observed by NMR. Structures of small macromolecules (less than 15 kD) can sometimes be resolved without special isotopic substitution of non-hydrogen atoms in the protein. Better data may be obtained from larger proteins if they are uniformly labeled by substituting the naturally abundant nuclear spin zero $^{12}$C and nuclear spin one $^{14}$N atoms with nuclear spin one-half $^{13}$C and $^{15}$N. In order to obtain NMR resonances sufficiently sharp for adequate resolution, the molecule must tumble rapidly. This typically limits the size of the molecule that can be analyzed with this method to about 30 kD. Also, the macromolecule must be soluble at high concentration (0.2-1 mM, 6-30 mg/ml) and stable for days without aggregation under the experimental conditions. However, the small molecule size limitation of NMR techniques eliminates its use with comparatively larger macromolecules. In addition, the use of NMR on combined molecules has often proven unreliable because of the inherent difficulty in distinguishing between the protons of the ligand and the protons of the small proteins. Accordingly, current NMR techniques are generally unsatisfactory for providing detailed atomic level information of the active sites of a macromolecule and the interaction of the ligand with those sites.

In contrast to solution NMR, single crystal diffraction experiments are used in an attempt to determine the structure of a macromolecule in a solid-state environment where the macromolecules have crystallized into a periodic three-dimensional array to form a macroscopic single crystal. The crystal is irradiated with a beam of radiation (often X-rays) and its diffraction properties measured as a function of sample orientation. Analysis of the resulting diffraction peaks is used to provide high-resolution structural data of macromolecules and macromolecule-ligand complexes.

Single crystal X-ray crystallography can be a powerful technique that can allow the determination of some secondary and tertiary structure of certain macromolecular targets. See, Erikson and Fesik, *Ann. Rep. in Med. Chem.*, 1992, 27, 271-289. It can be an expensive procedure and is often difficult to accomplish because of the need to grow large crystals of the macromolecule. Crystallization of most macromolecules is challenging and time consuming, often requiring specialized conditions that are quite different from those under which the molecule functions in vivo and is often considered to be as much an art as a science that can frequently end in failure. See, T. M. Bergfors, *Protein Crystallization Techniques, Strategies and Tips, a Laboratory Manual*, International University Line, La Jolla, Calif. 1999; N.E. Chayen, *Recent Advances in Methodology for the Crystallization of Biological Macromolecules*, J. Crystal Growth 198/199, 649-655 (1999). Furthermore, substantial quantities of the macromolecule may be consumed in the search for a set of conditions that allow the macromolecule to crystallize.

Another fundamental limitation on the use of single crystal methods is the ability to produce quantities of suitably diffracting single crystals of the macromolecule-ligand complex for analysis. One approach for making a single crystal of the macromolecule-ligand complex when a single crystal of the unbound macromolecule is already available is to soak the single crystal of the unbound macromolecule in a solution of the ligand. A significant complication of this approach is that the crystal may fracture when a ligand is introduced into the crystal to form the intended macromolecule-ligand complex of interest. Another complication of this method is that it may be difficult to achieve a uniform occupation of the ligand across the unit cells of the crystal. Moreover, binding may be inhibited by steric interference from intermolecular contacts within the crystal structure of the macromolecule.

An alternative method for making single crystals of the macromolecule-ligand complex is co-crystallization where the macromolecule-ligand complex is formed in advance of growing the single crystal. Although this approach has had some success in single crystal settings, co-crystallization typically requires a search for new optimal crystallization conditions for each ligand due to shifts in the solubility of the macromolecule-ligand complex. In addition, reactions between the macromolecule and ligand over the length of time required for single crystal growth may also interfere with crystallization. See, R. A. Palmer, *X-Ray Crystallographic Studies of Protein-Ligand Interactions* in Chapter 1 of *Protein-Ligand Interactions: Structure and Spectroscopy*, edited by S. E. Harding and B. Z. Chowdhry, Oxford University Press (2001). Accordingly, single crystal X-Ray crystallography often has limited application to the investigation of macromolecule-ligand complexes. Alternative methods for determining macromolecule-ligand structures that can circumvent the disadvantages of the solution NMR and single crystal diffraction methods are therefore of critical interest and substantial commercial value. Methods are greatly needed that allow one or more of the sites of interaction between the macromolecule and ligand and the structure of the macromolecule-ligand complex to be determined.

Another method for investigating the structure of simple crystals with small unit cells is powder diffraction crystallography. Powder diffraction crystallography differs fundamentally from the single crystal diffraction method because a polycrystalline sample of material rather than a single crystal is employed. In the powder diffraction method the sample is irradiated with a suitable beam of radiation such as X-rays, electrons or neutrons. The atoms in each crystallite of the irradiated sample form a three dimensional periodic array and consequently each crystallite behaves as a tiny three-dimensional diffraction grating for the incoming radiation. If the beam of radiation used is monochromatic, the diffracted beams from the aggregate of crystallites will form a series of concentric cones of radiation whose axes are centered on the direction of the incident beam. The very large number of crystallites that comprise the polycrystalline sample ensures that these cones are of uniform intensity that is proportional to the scattered intensity from an individual crystallite. The diffracted beams of radiation are measured as a function of angle, $2\theta$, between the incident and diffracted beams. It can be shown, with certain simplifying assumptions, that diffraction peaks may occur when the condition $$\lambda = 2d_{hkl} \sin(\theta),$$

is satisfied, where $\lambda$ is the wavelength of the radiation, $d_{hkl}$ is the inter-planar spacing between the Miller planes with indices h, k and l, and $\theta$ is the Bragg angle which measures the angle of reflection between the incident radiation and the Miller plane with indices h, k, l, a condition known as Bragg's law. The spacings between Miller planes in the crystal can be computed given a list of Bragg angles where diffraction peaks occur and the wavelength of radiation used in the experiment. Such spacings between Miller planes are sometimes referred to as "d-spacings" in the literature. In practice the diffraction peaks measured in a diffraction experiment are not infinitely sharp, as suggested by Bragg's law, but are broadened by factors such as the finite resolution of the diffractometer, the finite size of the crystallites in the sample, defects in the crystallites and the strains in the crystallites.

An important step in the interpretation of powder diffraction data is to identify possible space groups and lattice parameters of the sample. This may be achieved, for example, by recognizing that the diffraction profile corresponds to a material whose diffraction profile has been measured previously, or by the identification of an isostructural material of known structure. Alternatively the pattern may be indexed, by assigning h, k and l values to prominent peaks in the diffraction pattern, through the use of auto-indexing software, and likely values of the lattice parameters deduced. Several software packages for indexing of powder diffraction data are available including ITO, TREOR and DICVOL. Possible space groups of the crystal may be inferred by examining the diffraction pattern for the systematic absence of peaks in the powder diffraction pattern. See for example, A. K. Cheetham, *Ab Initio Structure Solution with Powder Data*, Chapter 15 of *The Rietveld Method*, Edited by R. A. Young, International Union of Crystallography, Oxford University Press (1993).

The periodic array of atoms in a crystal defines a periodic scattering density, $\rho(r)$, which is probed by diffraction experiments, $\rho(r)$ is periodic and it may be written as a Fourier sum over structure factors according to $$\rho(r) = \frac{1}{V} \sum_{hkl} F(h) \exp(-2\pi i (h \cdot r)),$$

where:
1. F(h) is a complex structure factor;
2. h is a reciprocal lattice vector equivalent to hkl;
3. V is the volume of the unit cell of the crystal; and
4. r is the location of interest within the unit cell of the crystal.

The complex structure factor F(h) may also be alternatively written in terms of a real amplitude, |F(h)|, and real phase, $\phi$(h), according to $$F(h) = |F(h)| \exp(i\phi(h)).$$

The intensities of peaks in both single crystal and powder diffraction experiments yield information on the amplitudes of the structure factors |F(h)|, but neither type of diffraction experiment directly yields the phase factors $\phi$(h). Unfortunately, reconstruction of the full periodic scattering density requires knowledge of the full structure factor including both phase and amplitude parts. The fact that phase factors are not directly measured in diffraction experiments creates a significant obstacle in the interpretation of diffraction data and is the origin of the phase problem in crystallography.

Computational techniques used in the analysis of powder diffraction profiles include the Rietveld method. See for example, R. A. Young, *The Rietveld Method*, International Union of Crystallography, Oxford University Press (1993). In Rietveld analysis the measured diffraction profile is simulated using an approximate starting model for the diffraction instrument and the sample, and it is in essence a curve fitting procedure. An objective function, M, that measures the difference between observed and calculated diffraction profiles is usually defined through $$M = \sum_i w_i (Y_{oi} - Y_{ci})^2$$

where:
1. $Y_{oi}$ is the observed intensity for the $i^{th}$ point in the diffraction pattern;
2. $Y_{ci}$ is the calculated intensity for the $i^{th}$ point in the diffraction pattern; and
3. $w_i$ is a weight often defined by $$w_i = \frac{1}{Y_{oi}}.$$

Subsequently, physical parameters of a model, such as atom positions, site occupancies and thermal motion parameters, the lattice parameters, phase compositions, crystallite sizes, profile parameters, etc. are adjusted so as to minimize the function M using a least squares optimization method. Additional parameters that may be adjusted include a scale factor, background terms to model diffuse scattering of radiation, and solvent terms to account for the effects of solvent molecules in the crystal. Rietveld programs usually offer flexibility in defining which parameters of the model should be optimized and enable the user to specify that refinements should be performed subject to constraints and restraints. For example, it may be possible to vary the site occupancies of a group of atoms subject to the constraint that the occupancies of all atoms in the group must remain equal. As another example, Rietveld programs may contain facilities for performing rigid body refinement where two or more atoms in the unit cell of the crystal are defined to form a rigid body and refinements are performed by allowing some or all of the translational and rotational degrees of freedom of the rigid body to vary. In another example, the objective function, M, may combine contributions from the powder pattern as described above and previously known stereochemical information such as bond lengths, bond angles, group planarities, volumes of chiral centers, torsion angle distributions and non-bonded contact distances. The extent to which the calculated profile is successful in reproducing the experimental pattern is measured by a number of numerical criteria of fit such as R-structure factor ($R_F$), R-pattern ($R_p$) and R-weighted pattern ($R_{wp}$). These numerical criteria of fit, which are generally referred to as R values, are described in more detail by R. A. Young, supra, and are well known to those skilled in the art of Rietveld refinement. Practical information on the application of the Rietveld method can be found in the article by L. B. McCusker, R. B. Von Dreele, D. E. Cox, D. Louër, and P. Scardi, *Rietveld Refinement Guidelines*, J. Appl. Cryst. 32, 36-50 (1999).

Diffraction in X-ray diffraction experiments takes place as a result of scattering of the X-rays by the electrons in the material under study. In neutron diffraction experiments neutrons are scattered by the atomic nuclei of the material. Consequently, the intensity of each diffraction peak in either experiment may be used to infer information about the distribution of the respective scattering density in the unit cell and scattering density maps, constructed by Fourier methods for example, may be used to view this density. Fourier analysis methods are widely used in the interpretation of diffraction data. For example, when a partial model of a crystal structure is available, for example from the molecular replacement method, it is often possible to obtain additional insights into the structure using a difference Fourier map. The difference Fourier map is constructed by combining structure factor amplitude and phase information from the model with observed structure factor amplitudes derived from the diffraction experiment. The difference Fourier map provides approximate information on the scattering density in the unit cell that is unaccounted for or placed in error by the partial structure. The difference Fourier map may therefore enable the positions of atoms in certain materials whose positions are unknown to be determined. Other types of Fourier maps are also known in the art. A second type of Fourier map is an OMIT map which enables tests to be performed to confirm the correct positioning of an atom or a set of atoms in a structural model. A third type of Fourier map, that does not require approximate phases, and that can be useful in determining the positions of strongly scattering atoms in the unit cell, is the Patterson map. Fourier maps are extensively discussed in G. N. Ramachandran and R. Srinivasan, *Fourier Methods in Crystallography*, Wiley, Interscience, New York (1970).

Implementations of various Fourier map calculations for powder diffraction data are available in public domain software programs such as the GSAS package (A. C. Larson and R. B. Von Dreele, (2001) *General Structure Analysis System (GSAS)*, Los Alamos National Laboratory Report LAUR 86-748).

Powder diffraction is frequently applied to identify such a material in a search and match procedure by comparing its diffraction profile against a database of diffraction profiles of known such materials. It is also often used to determine quantities such as the unit lattice parameters of crystals, the space groups of crystals, the relative abundance of phases within a sample and to obtain crystal structure information. A major disadvantage of the powder diffraction method, however, is that crystal structure analysis is most readily applicable to systems with small and simple unit cells. Protein structures were considered to be far too complex for any serious attempt to be made to extract detailed structural information, such as atom positions, with this approach.

Accordingly, a need exists for a speedy and efficient method of determining the three dimensional structure of macromolecules and macromolecule-ligand complexes without the limitation of growing large single crystals and that will allow ligand design or modifications that will enhance the biological or pharmacological properties of the ligand. The present invention satisfies that need, as well as others, and overcomes many of the deficiencies of previously attempted solutions.

BRIEF SUMMARY OF THE INVENTION

Deficiencies inherent in single crystal crystallography and NMR spectroscopy of macromolecule-ligand complexes are overcome by the present invention that generally comprises a method for providing atomic level, high resolution structures of macromolecules and macromolecule-ligand complexes using powder diffraction.

By way of example, and not of limitation, a preferred method for analysis of a macromolecule-ligand complex generally comprises the steps of 1) producing or otherwise acquiring a microcrystalline sample of a macromolecule in the absence of a ligand (unbound macromolecule) and a microcrystalline sample of a macromolecule-ligand complex prepared under similar conditions, 2) collecting powder diffraction data from each of the microcrystalline samples, and 3) analyzing the powder diffraction to identify, for example, the location of the macromolecule binding site, the location of the ligand binding site, the chemical nature of the binding sites, the orientation of the ligand in the binding site, and other structural information.

In one embodiment of the invention, microcrystalline samples are created from purified macromolecules that have been lyophilized prior to microcrystallization. The lyophilized macromolecules may be re-solvated with a buffer and a solvent and then physically agitated to produce microcrystallites. Samples of a microcrystallized macromolecule-ligand complex are preferably formed under the same conditions of pH, temperature, reagent concentrations and the like as those forming the samples of unbound macromolecules.

Preferred microcrystallites may be approximately 1 µm to approximately 10 µm in size and are preferably a substantially homogeneous collection. It is also preferred that the level of micro-strains and defect concentrations be sufficiently low to produce less than 0.1% broadening of the diffracted peaks in the measured pattern. Microcrystallites with these characteristics generally provide preferred powder diffraction data.

In an alternative embodiment, the ligand molecule is labeled to aid in the location of the ligand with respect to the binding site. In another embodiment, the ligand contains one or more heavy atoms that contribute strongly to the powder diffraction pattern in order to simplify the determination of the position of the heavy atom as well as in the determination of the binding site structure.

Once the diffraction data is collected it is analyzed. The unbound macromolecule diffraction pattern is preferably indexed to obtain unit lattice parameters and identify possible space groups. In a preferred embodiment, an approximate molecular model for the structure of the unbound macromolecule may be obtained from previous single crystal X-ray diffraction experiments, or from NMR experiments, or from homology models, or from theoretical modeling. The approximate model can assist in the analysis of the powder diffraction data including determining the orientation of the macromolecule in the unit cell to obtain an approximate crystallographic model of the unbound macromolecule.

As part of the analysis, the approximate crystallographic model of the unbound macromolecule is preferably subjected to a mathematical refinement using, for example, a combined Rietveld stereochemical restraint refinement. The refinement is accomplished in view of the diffraction data collected from the microcrystalline sample of the unbound macromolecule.

A difference Fourier map may also be produced from the diffraction data collected on the macromolecule-ligand complex using phases derived from the refined coordinates of the crystallographic model of the unbound macromolecule derived previously. Analysis of scattering density in a Fourier difference map, for example, will disclose the location and orientation of the ligand with respect to the macromolecule. Further refinement of the macromolecule-ligand complex structure may be accomplished, for example, with a combined Rietveld and stereochemical restraint refinement if necessary. In another embodiment of the invention, analysis of a density map is performed using computer graphics to visualize the density map in three dimensions. In yet another embodiment, analysis of the density map is performed using computer docking algorithms to obtain an optimal alignment between the ligand and the density map.

The results obtained by the use of the methods described and claimed herein allows a practitioner to observe the structure of the active site of the macromolecule, conformational changes that may be induced by ligand binding, and the conformation and orientation of the ligand within the active site or sites. The density maps are preferably of sufficient resolution that the amino acid side chains of the macromolecule that are involved with the particular interaction with the ligand, as well as the spatial orientation of the atoms or side groups in the ligand can be determined.

Once the mode of binding of the ligand within the active site of the macromolecule is determined, for example, it can be compared with the mode of binding of a different ligand within the same active site. The full range of macromolecule-ligand interactions can be explored by comparing the binding modes of progressively modified ligands. Such comparisons may also guide further modifications to the ligand that may enhance the desired biological or pharmacological properties of the ligand or macromolecule. It can be seen that the identification of, for example, the structure of the active site of the macromolecule, the locations of one or more atom to atom interactions in the active site of the macromolecule with the ligand, the determination of the relative distances between sites of interaction involved, conformational changes that may be induced by ligand binding, and ligand conformation and orientation information will allow the design of drugs, including small molecules or peptides, specifically configured to the active site of the macromolecule. These include blockers and antagonists, as well as drugs that function as agonists. Such agonists may be more effective than the natural ligand because they have a greater affinity for the macromolecule or has a greater half-life than the natural ligand. Non-peptide analogues may be designed that may be capable of being ingested rather than injected into the blood stream or have longer half lives in the body than the natural peptide ligand, among other things.

Additionally, agonists or antagonists to natural peptide ligands, for example, may be designed and tested that do not invoke feedback inhibition mechanisms or produce other side effects. Agonists or antagonists of pleiotropic ligands such as some signaling peptides, for example, may be developed that have only a single function or effect rather than several. Accordingly, one system may be manipulated without having an unwanted effect on other systems. It can also be seen that certain unobservable macromolecules that were previously not susceptible to single crystal analysis because they are incapable of large crystal growth or are too large for NMR spectroscopy are now open for analysis.

Thus, the inventions described and claimed herein include methods for determining macromolecule-ligand complex structures that comprise providing a sample of a polycrystalline macromolecule-ligand complex, obtaining powder diffraction data from the sample, and analyzing the diffraction data to generate a model structure of the macromolecule-ligand complex.

In certain embodiments, the methods for determining macromolecule-ligand complex structures may further include the steps of providing an approximate crystallographic model of the macromolecule unassociated with a ligand, and using the approximate crystallographic model in combination with the diffraction data from the sample of macromolecule-ligand complex to generate the model structure of the macromolecule-ligand complex.

In still other embodiments, the methods for determining macromolecule-ligand complex structures may include the steps of obtaining powder diffraction data from a sample of polycrystalline macromolecule unassociated with a ligand, and using the diffraction data in combination with the diffraction data from the sample of macromolecule-ligand complex to generate the model structure of the macromolecule-ligand complex.

Still other embodiments of the methods for determining macromolecule-ligand complex structures may include providing a molecular model of the macromolecule unassociated with a ligand, deriving an approximate crystallographic model of the macromolecule unassociated with a ligand in view of the powder diffraction data obtained from the macromolecule unassociated with a ligand and the molecular model, and refining the structure of the approximate crystallographic model in view of the powder diffraction data from the macromolecule unassociated with a ligand. In certain embodiments, the refining step may include conducting a combined Rietveld stereochemical restraint refinement on the approximate crystallographic model of the macromolecule unassociated with a ligand.

In other embodiments the methods for determining macromolecule-ligand complex structures may include creating a scattering density map from the structure of the refined crystallographic model of the macromolecule unassociated with a ligand and the powder diffraction data obtained from the sample of the macromolecule-ligand complex. The scattering density map may be analyzed to determine the binding location of the ligand within the macromolecule-ligand complex, for example, through computer analysis.

In other embodiments of the methods for determining macromolecule-ligand complex structures, the approximate crystallographic model may be derived from single crystal diffraction data for the macromolecule in the absence of a ligand.

In still other embodiments, the methods for determining macromolecule-ligand complex structures may include determining the binding location of the ligand within the macromolecule-ligand complex by a method that comprises obtaining phase data from a refined crystallographic model of the macromolecule unassociated with a ligand, producing a scattering density map from the diffraction data from the sample of macromolecule-ligand complex and from the phase data, providing a model of the ligand, and/or positioning the ligand model in the scattering density map. In one embodiment, the scattering density map may be a difference Fourier map. In another embodiment, the scattering density map may be improved by weighting a plurality of structure factors or by the application of maximum entropy principles.

In yet other embodiments, the methods for determining macromolecule-ligand complex structures may include identifying the sites of interaction between the atoms of the macromolecule and the atoms of the ligand, calculating the distances between the sites of interaction the atoms of the macromolecule and the atoms of the ligand, determining the structure of the ligand in the macromolecule-ligand complex, and determining the orientation of the ligand in the macromolecule-ligand complex.

In still other embodiments, the methods for determining macromolecule-ligand complex structures may include comparing the interaction of the ligand with the macromolecule with the interaction of a different ligand with the macromolecule. In other embodiments, the method further comprises comparing the interactions of progressively modified ligands with the macromolecule.

The invention is also directed to methods for rationally designing a ligand for binding to a macromolecule, comprising performing a powder diffraction according to the methods herein, selecting or designing one or more chemically modified analogs of the ligand for further testing based on the results of the method, and evaluating one or more activities or properties of the chemically modified analog or analogs.

The invention also features a method for determining the structure of a macromolecule-ligand complex, comprising providing a sample of polycrystalline macromolecule unassociated with a ligand, providing a sample of polycrystalline macromolecule-ligand complex, obtaining powder diffraction data from the samples, and analyzing the diffraction data to yield the structure of the macromolecule-ligand complex.

Additionally, the invention features a method for determining the structure of a macromolecule-ligand complex comprising obtaining powder diffraction data from a sample of a polycrystalline macromolecule-ligand complex, developing one or more molecular models of the macromolecule-ligand complex by docking one or more models of the ligand into one or more putative binding sites of a molecular model of the macromolecule unassociated with a ligand, developing one or more approximate crystallographic models of the macromolecule-ligand complex, and refining the structure of one or more of the approximate crystallographic models of the macromolecule-ligand complex in order to determine the structure of the macromolecule-ligand complex.

In certain embodiments, this method for determining the structure of a macromolecule-ligand complex further includes indexing the diffraction data collected from the sample of macromolecule-ligand complex.

In still other embodiments of this method for determining the structure of a macromolecule-ligand complex, one or more of the molecular model development, crystallographic model development, and structure refining steps is assisted by the use of a scoring function. The scoring function may further include the evaluation of non-bond interactions, the evaluation of hydrogen-bond interactions, and/or the evaluation of non-bond interactions and hydrogen-bond interactions.

In another embodiment, this method for determining the structure of a macromolecule-ligand complex may further include confirming the placement of the ligand as docked into the binding site of the determined structure of the macromolecule-ligand complex. The confirming step may comprise, for example, calculating an OMIT map to confirm the placement of the ligand as docked into the binding site of the determined structure of the macromolecule-ligand complex, and/or refining atom occupations on the ligand of the determined structure of the macromolecule-ligand complex. The refining may comprise, for example, performing a combined Rietveld and stereochemical restraint refinement. The refining may further comprise, for example, the consideration of R values.

In another embodiment of this method for determining the structure of a macromolecule-ligand complex, the development of one or more approximate crystallographic models of the macromolecule-ligand complex comprises use of a procedure selected from the group consisting essentially of rigid body Rietveld refinement, Monte Carlo sampling, and grid-based searching.

In another embodiment of this method for determining the structure of a macromolecule-ligand complex, the molecular model of the macromolecule unassociated with a ligand is derived from data selected from the group consisting essentially of NMR data, homology modeling data, threading modeling data, and single crystal diffraction data.

In other embodiments, these methods for determining the structure of a macromolecule-ligand complex may further comprise the development and/or use of more than one molecular model of the macromolecule-ligand complex, more than one model of the ligand, and/or more than one approximate crystallographic model of the macromolecule-ligand complex. Additionally, more than one model of the macromolecule unassociated with a ligand may be employed.

In certain embodiments of these methods for determining the structure of a macromolecule-ligand complex, the refining comprises performing a combined Rietveld and stereochemical restraint refinement and/or the consideration of R values.

In still other embodiments, these methods for determining the structure of a macromolecule-ligand complex may further include comparing the interaction of said ligand with said macromolecule with the interaction of a different ligand with said macromolecule. Still further, these methods may comprise comparing the interactions of progressively modified ligands with said macromolecule.

The invention also features a method for preparing a sample containing microcrystallites of a macromolecule-ligand complex suitable for analysis by X-ray powder diffraction comprising providing a quantity of substantially dehydrated macromolecules and a quantity of ligand molecules, and adding a liquid to the dehydrated macromolecules and the ligands, physically agitating the liquid, the dehydrated macromolecules and the ligands in order to form the microcrystalline sample of the macromolecule-ligand complex, and, placing the microcrystalline sample of the macromolecule-ligand complex on or in an X-ray powder diffraction sample holder or container. The dehydrated macromolecules may have been lyophilized, for example.

In another embodiment of this method for preparing a sample containing microcrystallites of a macromolecule-ligand complex suitable for analysis by X-ray powder diffraction, a quantity of a second ligand molecule is provided and the second ligand is added with the liquid, the ligands, and the dehydrated macromolecules prior to, during, or after the physical agitation. In still another embodiment, $D_2O$ may be added to the dehydrated macromolecules and the ligands.

In various embodiments this method for preparing a sample containing microcrystallites of a macromolecule-ligand complex suitable for analysis by X-ray powder diffraction, the liquid includes one or more nonaqueous solvents. In still other embodiments, for example, the liquid may comprise a buffer, a solvent and/or a salt solute. In other embodiments, the liquid may comprise one or more buffers and one or more aqueous or nonaqueous solvents. It may also comprise one or more buffers and one or more alcohols.

The invention also provides a method for determining the structure of a macromolecule comprising producing a sample of a polycrystalline macromolecule by a method comprising providing a quantity of substantially dehydrated macromolecules, and adding a liquid to the dehydrated macromolecules while physically agitating the macromolecules wherein the polycrystallites of the macromolecule are formed, collecting powder diffraction data from the sample of the polycrystalline macromolecule, and analyzing the diffraction data to yield the structure of the polycrystalline macromolecule.

In one embodiment of the method for determining the structure of a macromolecule, the analysis may comprise providing an approximate molecular model of the macromolecule, indexing the diffraction data from the macromolecule, deriving an approximate crystallographic model of the macromolecule in view of the approximate molecular model, indexing data and the diffraction data, and refining the structure of the approximate crystallographic macromolecule. The refining step may comprise, for example, conducting a combined Rietveld stereochemical restraint refinement on the approximate crystallographic model for the macromolecule. The source of the approximate molecular model may be selected from the group consisting essentially of homology models, threading models, single crystal experiment models and ab initio folding models.

In another embodiment of method for determining the structure of a macromolecule, the pH of the mixture of the liquid and the dehydrated macromolecules is from about pH 3 to about pH 9. In still another embodiment, the method for determining the structure of a macromolecule may comprise changing the temperature of the mixture of the liquid and the dehydrated macromolecules to promote crystallization of the macromolecule from the mixture. In another embodiment the physical agitation step of the method for determining the structure of a macromolecule may comprise grinding the mixture of the liquid and the dehydrated macromolecules within a grinding device.

The invention also features a method for determining the structure of a macromolecule-ligand complex comprising producing a sample of a polycrystalline macromolecule-ligand complex, the sample produced by a method comprising, providing a quantity of substantially dehydrated macromolecules and a quantity of ligand molecules, and adding a liquid to the dehydrated macromolecules and the ligand molecules while physically agitating the macromolecules and the ligands, wherein the polycrystallites of the macromolecule-ligand complex are formed, producing a sample of a polycrystalline macromolecule, the sample produced by a method comprising, providing a quantity of substantially dehydrated macromolecules, and adding a liquid to the dehydrated macromolecules while physically agitating the macromolecules, wherein the polycrystallites of the macromolecule are formed, collecting powder diffraction data from the sample of the macromolecule and the sample of macromolecule-ligand complex, and analyzing the diffraction data to yield the structure of the macromolecule-ligand complex. In another embodiment, the method may further comprise comparing the interaction of the ligand with the macromolecule with the interaction of a different ligand and the macromolecule. In still another embodiment, the dehydrated macromolecules and/or the ligand have been lyophilized.

The invention also features a method for determining the previously unknown structure of a macromolecule, comprising providing a sample of a polycrystalline macromolecule, obtaining powder diffraction data from the sample, and analyzing the diffraction data to generate a model structure of the macromolecule. In one embodiment, this method may further comprise providing an approximate molecular model of the macromolecule, and using the approximate molecular model in combination with the diffraction data from the sample of macromolecule to generate the model structure of the macromolecule. In another embodiment, the method may further comprise providing an approximate molecular model of the macromolecule, indexing the diffraction data from the macromolecule, deriving an approximate crystallographic model of the macromolecule in view of the approximate molecular model, indexing data and the diffraction data, and refining the structure of the approximate crystallographic model of the macromolecule. The refining step may comprise, for example, conducting a combined Rietveld stereochemical restraint refinement on the approximate crystallographic model of the macromolecule.

In another embodiment, the method for determining the previously unknown structure of a macromolecule may further comprise providing an approximate molecular model of one or more fragments of the macromolecule, indexing the diffraction data from the macromolecule, and, deriving an approximate crystallographic model of the of macromolecule in view of the approximate molecular model of the one or more fragments of the macromolecule in view of the indexing data and the diffraction data. This method may, still further, comprise creating a scattering density map from the approximate crystallographic model of the macromolecule and the powder diffraction data obtained from the sample of the macromolecule, and, using the scattering density map to perform structure completion. Additionally, the method may include refining the structure of the approximate crystallographic model of the macromolecule. This refining may be accomplished, for example, by conducting a combined Rietveld stereochemical restraint refinement on the structure completion model of the macromolecule.

For use in the method for determining the previously unknown structure of a macromolecule, the sample of polycrystalline macromolecule-ligand complex may be obtained by a method comprising providing a solution of the macromolecule-ligand complex, and, inducing precipitation of the macromolecule-ligand complex. In one embodiment, precipitation may be induced by addition of a precipitant selected from the group consisting essentially of a salt, an organic solvent, deionized water, a dye, and a polymer. In another embodiment, precipitation may be induced by physical means such as, for example, evaporation, centrifugation, change in pH, or change in temperature. In still other embodiments, the solution of the macromolecule-ligand complex may contain one or more ingredients selected from the group consisting essentially of salts, buffers, alcohols, polyglycols, detergents, lipids, and nucleating agents.

The invention also features a method for preparing a sample containing microcrystallites of a macromolecule suitable for analysis by X-ray powder diffraction, comprising providing a quantity of substantially dehydrated macromolecules, adding a liquid to the substantially dehydrated macromolecules, physically agitating the mixture in order to form the sample containing microcrystallites, and, placing the microcrystalline sample on or in an X-ray powder diffraction sample holder or container. The invention further includes a microcrystalline sample of a macromolecule on an X-ray powder diffraction sample holder produced according to this method. The invention also includes a microcrystalline sample of a macromolecule in an X-ray powder diffraction sample container produced according to this method. The invention further features a process for determining a high-resolution structure of a macromolecule, which comprises subjecting a sample produced in accordance with this method to X-ray powder diffraction, and analyzing the data obtained to obtain the high-resolution structure of the macromolecule.

In other embodiments of the methods for preparing a sample containing microcrystallites of a macromolecule suitable for analysis by X-ray powder diffraction, the liquid may be selected from the group consisting essentially of, for example, a buffer, a solvent, and a salt solute. In still other embodiments, the liquid may comprise a combination of one or more buffers and one or more solvents. In further embodiments, the liquid may comprise, for example, a combination of one or more buffers and one or more alcohols. Additionally, the liquid may comprise a nonaqueous solvent, or a combination of one or more nonaqueous solvents and one or more buffers.

In still other embodiments of the methods for preparing a sample containing microcrystallites of a macromolecule suitable for analysis by X-ray powder diffraction, the pH of the mixture of the liquid and the substantially dehydrated macromolecules is about pH 3 to about pH 9.

In yet other embodiments of the methods for preparing a sample containing microcrystallites of a macromolecule suitable for analysis by X-ray powder diffraction, the methods may further comprise changing the temperature of the mixture of the liquid and the substantially dehydrated macromolecules to promote crystallization of the macromolecule.

In still further embodiments of the methods for preparing a sample containing microcrystallites of a macromolecule suitable for analysis by X-ray powder diffraction, the physical agitation may comprise grinding the mixture within a grinding device. The grinding device may comprise a mortar and pestle.

In other embodiments, the methods for preparing a sample containing microcrystallites of a macromolecule suitable for analysis by X-ray powder diffraction may further comprise mixing a ligand with the substantially dehydrated macromolecules prior to adding the liquid.

In yet other embodiments of the methods for preparing a sample containing microcrystallites of a macromolecule suitable for analysis by X-ray powder diffraction, the methods may additionally comprise mixing a ligand with the sample containing microcrystallites prior to placing the microcrystalline sample on or in an X-ray powder diffraction sample holder or container in order to obtain a microcrystalline sample of a complex of the macromolecule and the ligand.

The invention also features a method for preparing a sample containing microcrystallites of a macromolecule suitable for high resolution analysis by X-ray powder diffraction, comprising providing a solution of macromolecules, inducing precipitation of macromolecules, placing the microcrystalline sample on or in an X-ray powder diffraction sample holder or container. In another embodiment, the invention features a microcrystalline sample of a macromolecule on an X-ray powder diffraction sample holder produced according to this method. In yet another embodiment, the invention features a microcrystalline sample of a macromolecule in an X-ray powder diffraction sample container produced according to this method. In any of these methods, the dehydrated macromolecules may have been lyophilized.

The macromolecule in any of the methods described and claimed herein may be selected from the group consisting essentially of peptides, fragments of peptides, proteins, fragments of proteins, and nucleic acids. Protein macromolecules include, for example, a receptor or enzyme or one or more fragments of a receptor or enzyme.

The ligand in any of the methods described and claimed herein may be selected from the group consisting essentially of peptides, fragments of peptides, proteins, fragments of proteins, nucleic acids, and small organic molecules.

In various embodiments of any of the methods described and claimed herein the radiation source of the diffraction data of in any of the methods described and claimed herein may be X-rays. The powder diffraction data is preferably obtained from x-ray diffraction using a synchrotron as a source of X-rays. However, it will be understood that essentially any conventional source of X-rays may be used as a source. Alternatively, the powder diffraction measurements may also be obtained using neutrons.

An object of the invention is to provide a method for determining structures of macromolecules, macromolecular-ligand complexes and macromolecular multiple ligand complexes using powder diffraction techniques.

Another object of the invention is to provide a method for determining atomic level structures of macromolecules, macromolecular-ligand complexes and macromolecular multiple ligand complexes using powder diffraction techniques.

Another object of the invention is to provide a method for identifying the structure of an active site or sites of a macromolecule.

Another object of the invention is to provide a method for identifying the conformation and orientation of a ligand and the portions of the ligand that interact with the active site of a macromolecule and determine spatial relationships.

Another object of the invention is to provide a method for identifying conformational changes in a macromolecule that are associated with the binding of a ligand or ligands.

Still another object of the invention is to provide a method for studying nucleic acid-protein interactions, protein-protein interactions and other interactions that may be useful in the overall understanding and treatment of disease or the advancement of science.

Yet another object of the invention is to provide methods for producing microcrystalline samples of a molecule, a macromolecule or a macromolecule-ligand complex that are suitable for powder diffraction studies.

Yet another object of the invention is to provide a method for producing microcrystalline powder samples suitable for powder diffraction, including samples obtained using lyophilized macromolecules as a starting material.

Further objects and advantages of the invention will be understood from the practice thereof, as well as from the following portions of the specification, wherein a detailed description has been provided for the purpose of describing, for example, preferred embodiments of the invention, which is limited only by the scope of the appended claims.

BRIEF DESCRIPTION OF THE DRAWINGS

The invention will be more fully understood by reference to the following drawings that are for illustrative purposes only.

DETAILED DESCRIPTION OF THE INVENTION

Figure 1:
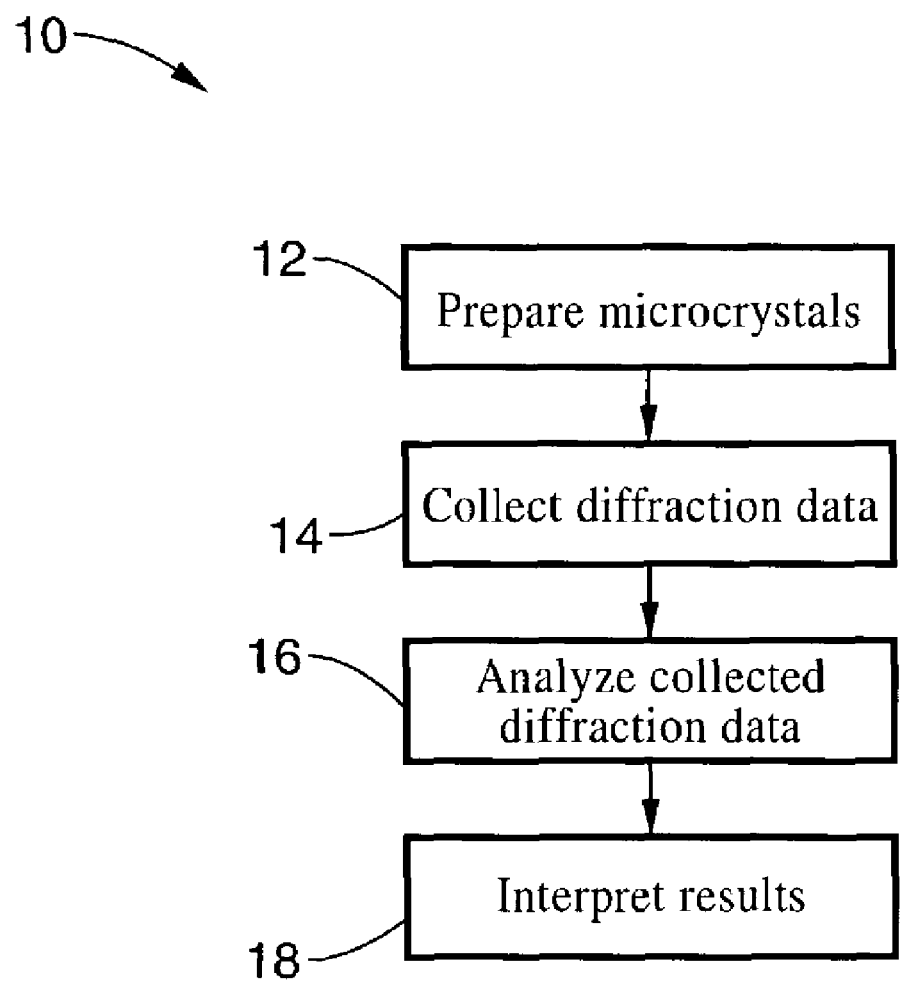
FIG. 1 is a flowchart of method steps according to one embodiment of the present invention for analyzing a macromolecule-ligand complex.

Referring more specifically to the drawings, for illustrative purposes one embodiment of the present invention is depicted in the methods generally shown in FIG. 1 through FIG. 9. It will be appreciated that the methods may vary as to the specific steps and sequence, without departing from the basic concepts as disclosed herein. The steps depicted and/or used in methods herein may be performed in a different order than as depicted andlor stated. The steps are merely exemplary of the order these steps may occur. The steps may occur in any order that is desired, such that it still performs the goals of the claimed invention. All documents including all described or cited herein are expressly incorporated by reference into the disclosure as though set forth in full.

The present invention provides a method of producing high-resolution structural imaging of macromolecules or macromolecule-ligand complexes. The term macromolecule-ligand complex refers to certain macromolecules that are known in nature or shown to specifically interact with other molecules or macromolecules. The various molecules or macromolecules that interact or associate with such macromolecules are termed ligands herein. Macromolecules may include, but are not limited to, enzymes, proteins, glycoproteins, antibodies, oligonucleotide sequences of RNA or DNA, or the like. The macromolecule-ligand complex is the combination of the macromolecule and one or more ligands. The points of interaction or association between the macromolecule and the ligand are referred to as active sites or binding sites. While macromolecule-ligand associations may include binding events ranging from the formation of a bond to van der Waals forces etc., the terms bound or unbound refers to any association between macromolecule and ligand, for purposes of illustration.

As described and claimed herein, the structures of a macromolecule-ligand complex are identified and evaluated by measuring the powder diffraction pattern of the macromolecule-ligand complex using, for example, X-ray powder diffraction.

Importantly, the invention does not rely upon the creation of large single crystals for analysis. In one embodiment of the invention, computational analysis of the diffraction pattern is combined with information about the structure of the macromolecule in the absence of the ligand to determine, for example, the location of the binding site of the ligand on the macromolecule. The method of the present invention may also be used to obtain, for example, the three-dimensional structure of the combined complex, as well as to identify the nature of the molecular interactions between the macromolecule and the ligand, the chemical make-up of the macromolecule and ligand binding sites, and conformational changes that may take place in the macromolecule and ligand upon complex formation.

Information derived in this process can be combined with other information to optimize the properties of a ligand as a drug. For example information on factors such as the dissociation constant of the macromolecule-ligand system, toxicity of the ligand and manufacturing costs of the ligand can be combined with structural information by those skilled in the art of drug discovery to guide the selection of changes to a ligand to improve one or more characteristics of the ligand as a drug.

Turning now to FIG. 1, the steps according to a preferred embodiment of the present method for determining and evaluating the structures of macromolecule-ligand complexes are illustrated. At block 12, samples of microcrystalline macromolecule are provided or prepared for powder diffraction and analysis. In a preferred embodiment of the invention, two microcrystalline samples of the macromolecule are provided. The first sample comprises a macromolecule-ligand complex (ML) where one or more ligands or putative ligands is present. The second sample comprises unbound macromolecule (UM), for example, a macromolecule in the absence of one or more binding ligands or putative binding ligands.

It is preferred that the conditions used in preparing the two samples are as similar as possible (including, for example, pH, salt concentration, mechanical handling of samples, solvents, etc,) so as to minimize differences between the crystalline arrangement of the macromolecules in the two samples. In an alternative embodiment only a sample of the macromolecule-ligand complex is prepared.

At block 14, high-resolution powder diffraction patterns are collected from the samples. Diffraction may be accomplished with X-rays or neutrons, or electrons, with X-rays being the preferred source of radiation for producing diffraction data. Synchrotron sources for the X-rays are particularly preferred as are X-rays from sources with high intensity, low beam divergence, provide flexibility in the choice of wavelength used in the diffraction experiment and can be configured to provide diffraction patterns with narrow peak width.

The powder diffraction data are then analyzed as represented by block 16. In a preferred embodiment, the analysis includes subjecting the model obtained using diffraction data of the unbound macromolecule to at least one combined Rietveld and stereochemical restraint refinement starting from an approximate molecular model of the macromolecule to obtain optimal atomic coordinates and structure factors. These structure factors are used in the analysis of the macromolecule-ligand diffraction data to preferably produce a difference Fourier map to locate and orient the ligand with respect to the macromolecule in three-dimensional space. The macromolecule-ligand complex is then preferably subjected to at least one combined Rietveld and stereochemical restraint refinement.

The results are then interpreted at block 18 to determine, for example, the location and structure of the active site or sites on the macromolecule the orientation of the ligand within the active site(s) of the macromolecule, and/or the molecular components of the ligand that bind to the macromolecule. The mode of interaction of the ligand and the amino acid side chains of the macromolecule (where the macromolecule is a protein or peptide) that are involved in the interaction for example, may then be used to guide the possible modification of the ligand to enhance the desired biological or pharmacological properties of the ligand. In addition, the binding of a modified ligand can be correlated or otherwise indexed to activity data in an effort to identify and understand those portions of the molecule that are responsible for ligand binding and/or activity.

Figure 2:
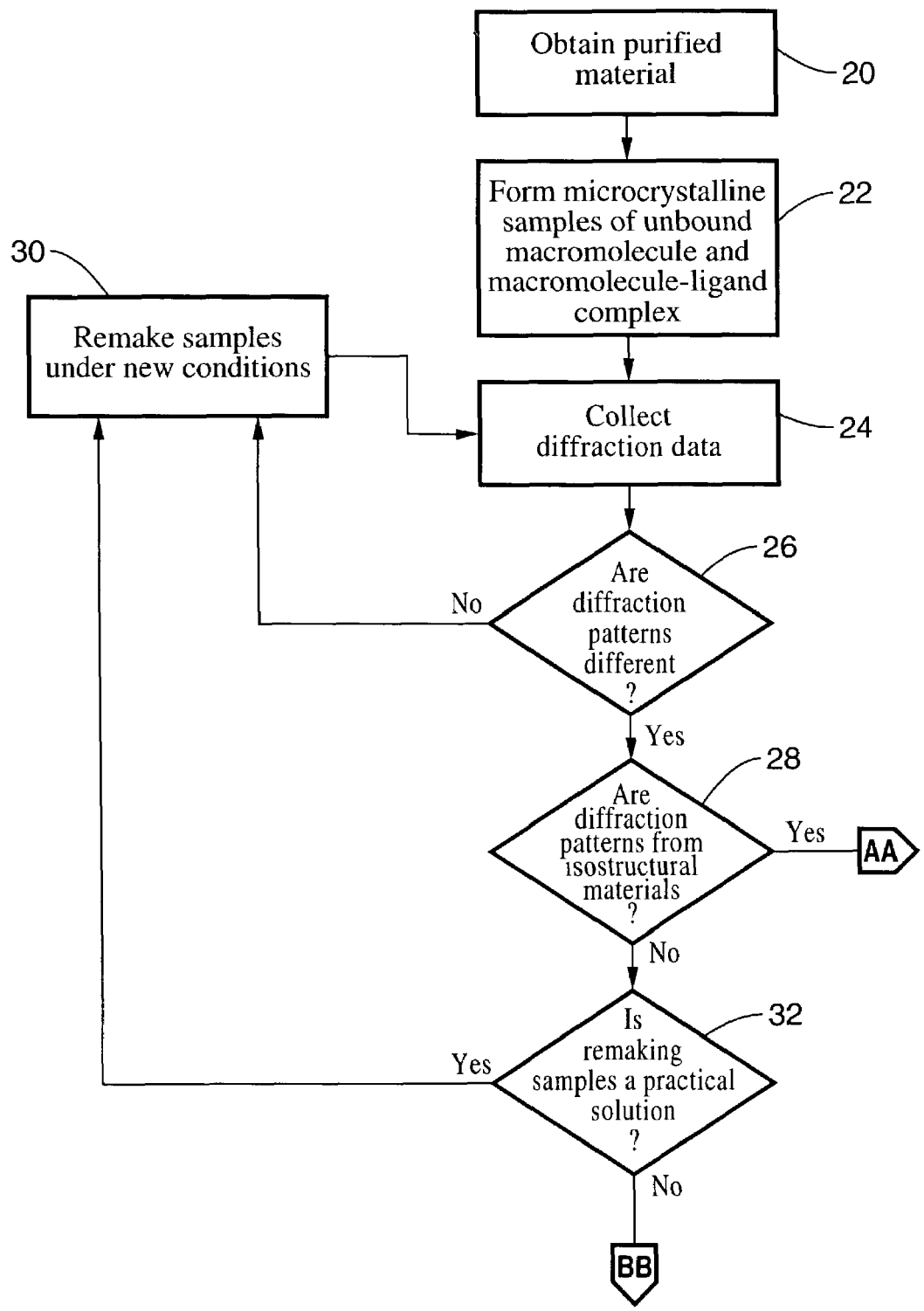
FIG. 2 is a flowchart of sample preparation and powder diffraction collection substeps according to one embodiment of the present invention.
Figure 3:
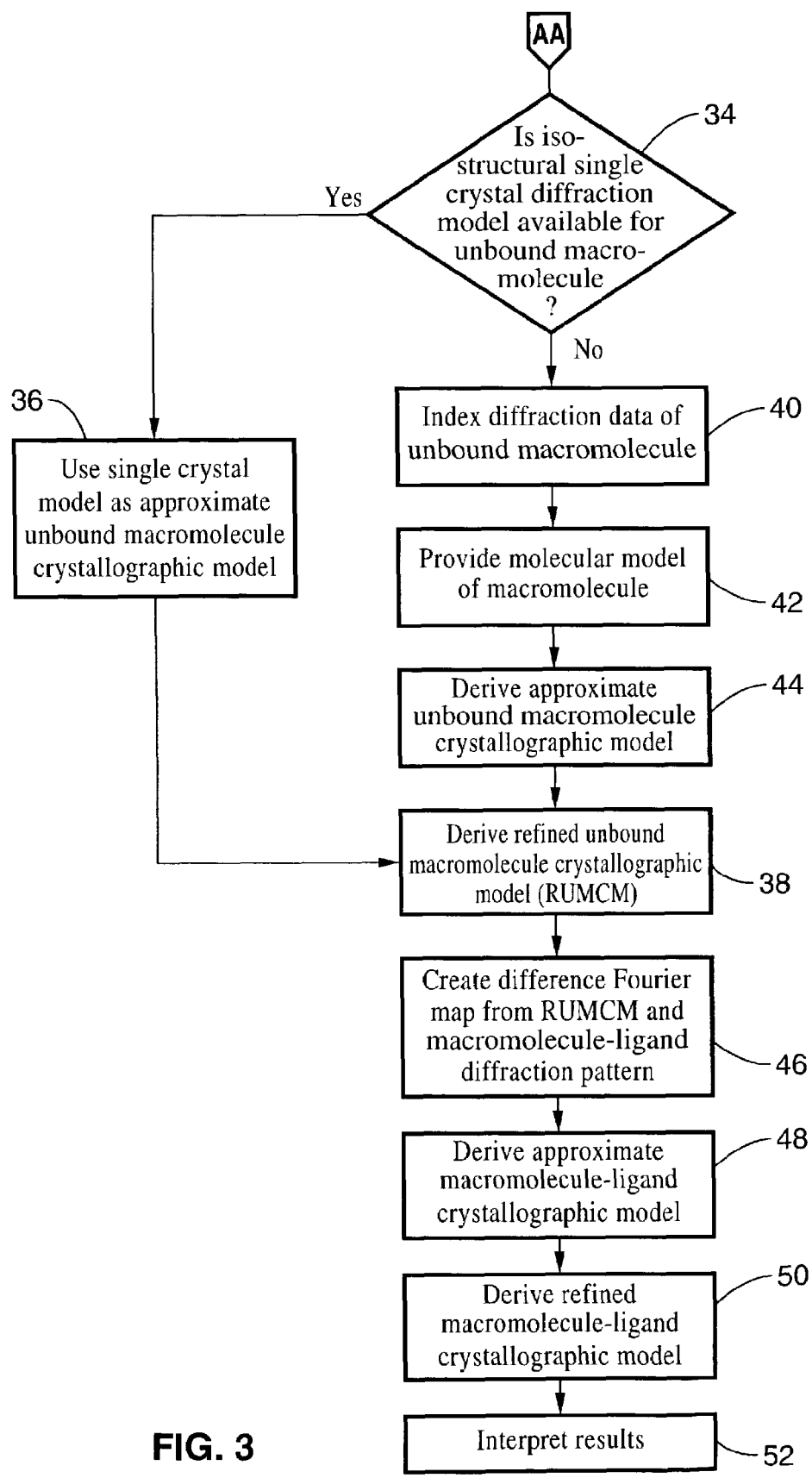
FIG. 3 is a flowchart of analysis and results interpretation substeps according to one embodiment of the invention.
Figure 4:
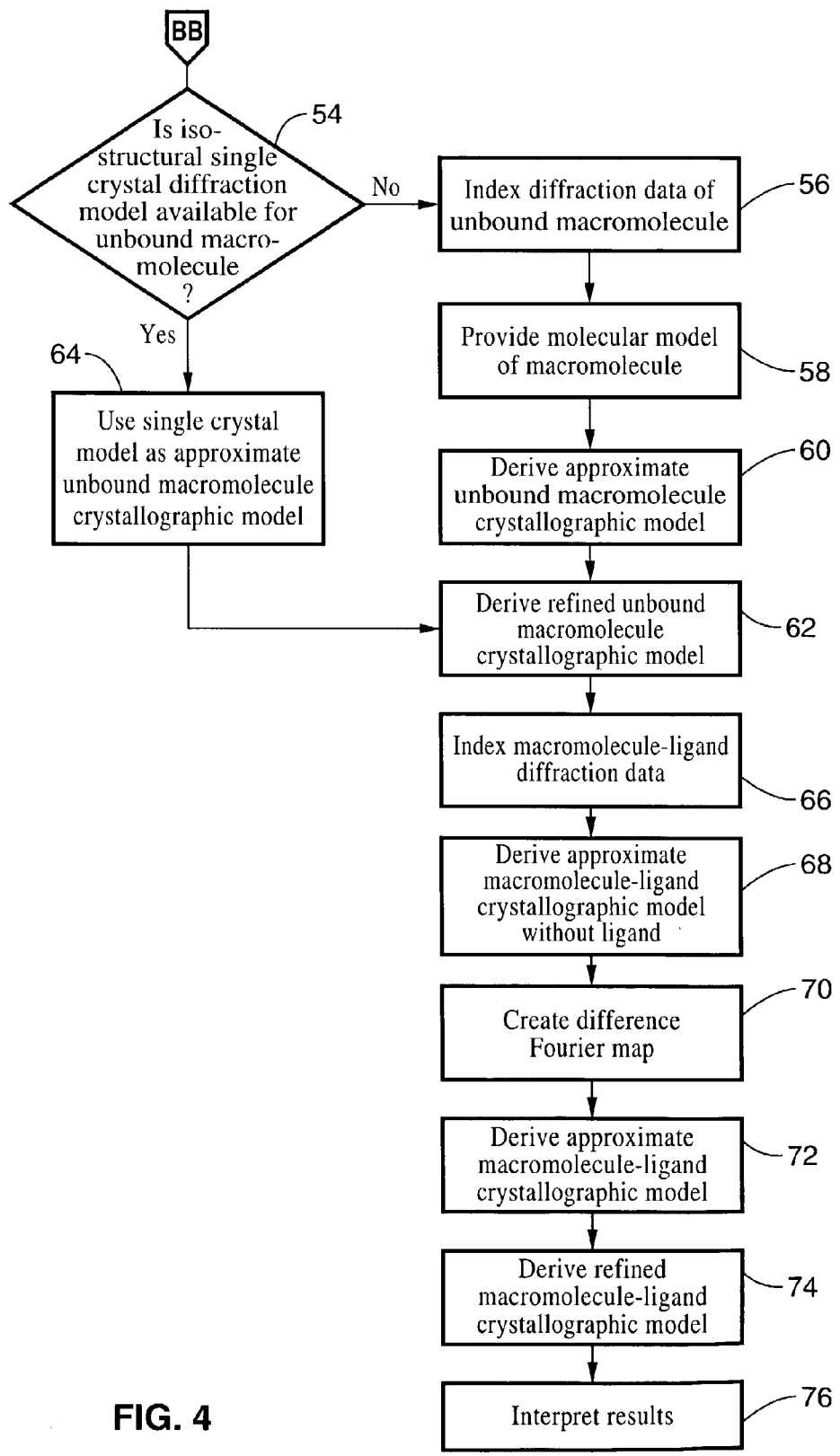
FIG. 4 is a flowchart of an alternative subset of method steps according to one embodiment of the present invention that are used when isostructural samples are not available.

Referring also to FIG. 2, FIG. 3 and FIG. 4, the steps according to one embodiment of the method for providing high-resolution atomic scale macromolecule-ligand structures is shown. The figures reflect, according to a series of steps, a data collection and analysis method under preferred conditions. However, it will be appreciated that the method of the present invention may be implemented in a variety of ways without departing from the teachings of the present invention.

The first step in a preferred production of microcrystals is to obtain a sufficient quantity of purified macromolecule for crystallization as indicated in block 20 of FIG. 2. Preferably, a quantity of macromolecule is provided that will produce between approximately 0.0001 to approximately 10.0 cubic millimeters of microcrystals for analysis in the powder diffractometer.

The macromolecule need not be 100% pure in order to produce microcrystals. Some impurities can in fact act beneficially as crystallization nuclei. However, it should be understood that the purity of the starting material is preferably sufficient to ensure that the resulting microcrystalline powder produces a high quality diffraction pattern. It is also preferred that the sample produced in the preparation process comprises a single crystalline phase. In a preferred embodiment of the invention the size of the microcrystallites are approximately 1 µm to approximately 10 µm across and micro-strain levels and defect concentrations are low enough to produce a less than 0.1% broadening of the diffraction peaks in the measured pattern. It is thus understood that the microcrystalline samples may contain an ensemble of many microcrystallites that are preferred to be of a single phase.

The samples of crystalline macromolecule and macromolecule-ligand complex formed in the step at block 22 may be prepared by the use, for example, of one of the following methods 1) the grinding of lyophilized macromolecule, 2) precipitation from solution and 3) grinding of single crystals to sufficient size. Other sample preparation methods may be used so long as they result in samples having the characteristics desired for purposes of experiment or analysis.

Each of these sample preparation methods may in many cases be assisted with the use of sample preparation liquids comprising, for example, one or more aqueous or non-aqueous solvents. It is understood that such solvents may include dissolved reagents such as salts, buffers, alcohols, polyglycols, detergents, lipids, nucleating agents and the like alone or in combination. The selection of sample preparation liquid and other crystallization conditions will depend on the nature of the macromolecule and ligand under consideration.

In a preferred embodiment, lyophilized macromolecule is used as a starting material. The removal of the water molecules that are usually associated with the macromolecule by lyophilization is believed to make the material particularly susceptible to the formation of microcrystals. In this approach to the formation of a microcrystalline sample, lyophilized macromolecule may be ground by hand, for example, with a mortar and pestle, or by a machine or in a microscale machine with a sample preparation liquid. It is preferred that the crystallization occur rapidly under substantially homogeneous conditions to form a mixture of uniform microcrystallites. The formation of a microcrystalline suspension of the macromolecule may be indicated by the liquid acquiring a cloudy appearance. The suitability of the microcrystalline sample for analysis may be confirmed by the appearance of sharp peaks in the diffraction pattern produced at block 24 of FIG. 2.

An alternative approach for producing microcrystalline samples suitable for powder diffraction is through precipitation of the macromolecule from a sample preparation liquid. Precipitation may be induced by adjusting the degree of saturation of a solution of the macromolecule by chemical or by physical means. For example the degree of saturation of the solution may be adjusted by the addition of a precipitants selected, for example, from one or more of salts, organic solvents, polymers, sulfonic dyes or deionized water. In addition, the degree of saturation may be adjusted by making changes in temperature, changes in pH or by making adjustments in the concentration of the macromolecule effected, for example, by solvent evaporation or by centrifugation of the macromolecule solution.

In a third alternative approach, microcrystalline samples may be prepared from large single crystals. Typically, samples are prepared by grinding large single crystals in the presence of a sample preparation liquid in order to prevent drying of the macromolecules. See for example, R. B. Von Dreele, P. W. Stephens, G. D. Smith and R. H. Blessing, *The First Protein Crystal Structure Determined from High-resolution X-ray Powder Diffraction Data: A Variant of $T_3R_3$ Human Insulin-Zinc Complex Produced by Grinding*, Acta Cryst. D56, 1549 (2000).

With respect to the formation of microcrystalline samples of the macromolecule-ligand complex step at block 22 of FIG. 2, two approaches are preferred. The first approach is through co-crystallization, where the macromolecule and ligand are complexed before crystallization commences, or as crystallization proceeds, and microcrystals of the entire complex are formed. It is understood that the cocrystallization approach may be used in conjunction with any of the three sample preparation methods discussed above for producing crystals of the unbound macromolecule. A preferred method for making microcrystalline samples of the macromolecule-ligand complex via co-crystallization is to grind lyophilized macromolecule in the presence of a solvent containing buffers, salts and the ligand. An alternative method for making microcrystalline samples of the macromolecule ligand complex via co-crystallization is to precipitate microcrystals from a solution containing the macromolecule-ligand complex. A third alternative method is to use co-crystallization to grow single crystals of the macromolecule-ligand complex and subsequently form a microcrystalline sample by mechanically grinding the single crystals.

In the second approach to the formation of microcrystalline samples of the macromolecule-ligand complex, the ligand is allowed to diffuse into a microcrystalline sample of the unbound macromolecule by soaking the microcrystalline sample in a solution containing the ligand. A microcrystalline sample of the unbound macromolecule may be made, for example, by any of the three previously described methods. In a preferred embodiment of the invention the microcrystalline sample of the unbound macromolecule is formed by either the grinding of lyophilized macromolecule prior to soaking the sample in a solution containing the ligand. An advantage of this ligand diffusion approach to sample preparation is that the geometry of the macromolecule in the crystal is likely to be similar in the unbound and complexed form, possibly facilitating subsequent analysis of diffraction data. The small dimensions of microcrystals may enable high occupation of the ligand in a microcrystalline sample to be achieved more quickly and more easily than is the case with a large single crystal. Furthermore, the rapid formation of microcrystals through the preferred methods allows the possible exploration of initial macromolecule-ligand complex formation under a wide variety of conditions that are not accessible to slow-soaking or single crystal growth procedures. Polycrystallization of macromolecules and macromolecule-ligand complexes through the preferred method of crystallizing or cocrystallizing lyophilized starting material appears to produce a powder of essentially defect free crystallites that are a few microns across and comprise only a few hundred macromolecule unit cells across each edge. Powder diffraction patterns from these microcrystalline materials provide sharp peaks and the determination of detailed structural features of the macromolecule-ligand interactions may be obtained. In some settings, the location and electron density contributions of solvent atoms or certain atoms of the ligand may be assisted by the placement of heavy atoms in the crystal structure. Such heavy atoms provide characteristic electron density contributions that may assist in the placement of certain atoms of the ligand or atoms of the macromolecule or atoms of solvent molecules. Heavy atoms may typically include the transition metals, the lanthanide series and Uranium. Some Noble gases have been used under pressure to soak into crystals through solvent channels to bind to crystallized protein molecules. Other useful molecules may include $D_2O$ and the like.

The preparation of exemplary microcrystalline samples of a macromolecule and/or a macromolecule-ligand complex by grinding of the lyophilized macromolecule with suitable solutions in the presence and absence of the ligand is set forth in the Examples 1 through 3 herein. Prior to the diffraction step 24 of FIG. 2, it is preferred that the microcrystalline samples be placed in a sample holder and be compacted. Samples may, for example, be placed in a capillary sample holder, designed for powder diffraction experiments. In a preferred embodiment, the sample is compacted by placing the capillary containing the sample in a standard laboratory centrifuge. In a preferred embodiment of the invention the vigor and duration of the centrifuging is sufficient to draw the microcrystals out of suspension to form a dense powder at the bottom of the capillary. In another preferred embodiment of the invention, the capillary may be set upright and compaction of the microcrystallites allowed to occur under the force of gravity.

It is also preferred that the sample is prepared such that solvent saturated in the macromolecule be maintained around the microcrystallites of the sample to minimize the possibility that microcrystallites will dry in the course of diffraction measurements. In a preferred embodiment of the invention, where the sample holder is a glass capillary, this may, for example, be accomplished by removing excess solvent from the capillary and flame sealing the capillary to prevent evaporation of the remaining solvent. In another preferred embodiment of the invention the sample holder may be sealed with a malleable material such as modeling clay.

In another preferred embodiment of the invention the microcrystallites are freed of excess solvent and contained within a capillary in the presence of sufficient solvent to prevent drying out of the microcrystallites. Although the use of a glass capillary is preferred, it will be understood that other methods of containing the sample in the beam are contemplated. For example, the capillary could be made of "plastic" or fused silica or even carved from single crystal quartz. Likewise the sample could be trapped on a Millipore filter or other filter material.

A typical experiment using an X-ray synchrotron source may use a glass capillary with a diameter of 1.5 mm and a length of 8.0 mm that may thus include on the order of about 10 mg of macromolecule. However, it will be understood that the quantity of microcrystalline powder that is required for the diffraction analysis will vary depending on factors such as the type of X-ray source and diffractometer that is used, and whether steps have been taken to minimize the quantity of macromolecule consumed in the experiment.

After suitable microcrystalline powders are obtained of the unbound macromolecule and macromolecule-ligand complex, powder diffraction data is collected from the samples is shown at block 24 of FIG. 2.

Diffraction data may be generated several ways including with X-rays and neutrons as shown in Examples 1, 2 and 3 herein. X-rays and neutrons are the two most widely used forms of radiation in powder diffraction experiments. X-rays may be generated in the laboratory using an X-ray tube or rotating anode source or they may be generated at a specialized facility with a synchrotron. Typically, X-rays produced in a laboratory source are generated by firing electrons at a metal anode. Electrons striking the anode cause excitation of core electrons of the metal into excited states, which subsequently transition back to the core levels with simultaneous emission of X-rays. Most typically copper is used as the anode but other metals such as iron, cobalt, molybdenum and silver may be used. In the case of synchrotrons a beam of charged particles, such as electrons, traveling at close to the speed of light is contained within a ring. X-rays are emitted as the direction of the particle beam is changed for example when the particles are accelerated towards the center of the ring so as to maintain their orbit.

The advantages of synchrotron radiation in X-ray powder diffraction experiments include the high intensity of radiation available synchrotron sources, the fact that beam divergence is very low resulting in sharp diffraction features and that the wavelength of radiation can be easily tuned. X-ray sources are discussed further in the book by J. Drenth, *Principles of Protein X-ray Crystallography*, Springer Advanced Texts in Chemistry, Springer (1999).

The wavelength of X-rays to be used in the experiment is a trade off between a number of factors and the selection of wavelength depends on the source of X-rays and the diffractometer used in the experiment. In the case of synchrotron X-ray sources the wavelength of X-rays used in the experiment may be adjustable through the use of suitable monochromators. Sample radiation damage is minimized by the use of shorter wavelength X-rays. However it is also desirable to obtain data of high resolution. Short wavelength radiation compresses the range of Bragg angle in which useful diffraction data occurs and selecting a too short wavelength may compromise the resolution of the experiment.

Synchrotron beam time is a valuable resource given the high capital and operational costs of synchrotrons. In some synchrotrons the ring is recharged with electrons on a periodic basis. It may be desirable to ensure that no recharging events occur in the course of collecting the diffraction pattern as the recharging process may cause discontinuities in the diffraction pattern, complicating subsequent data analysis. It may therefore also be desirable to minimize the amount of time that the experiment will take by working at a wavelength where the beam line is capable of providing an intense beam of X-rays both to minimize cost of the experiment and to ensure that the intensity of the X-rays is such that the diffraction experiment can be completed in the period between two recharging events.

Referring also to Example 1 and Example 2, in the case of diffraction experiments carried out on the macromolecule lysozyme at the X3b1 beam line of the National Synchrotron Light Source at Brookhaven National Laboratory it was determined that X-rays with a wavelength of about 0.7 Å provided a reasonable compromise in the tradeoff between these factors. Recharging events took place about once every 12 hours while the experiments were being performed. About 6,000 measurements were found to be needed in the scan over Bragg angles. The intensity of the beam was such that adequate counting statistics could be obtained with a measurement time of a few seconds for each sampled Bragg angle enabling the entire pattern on one sample to be collected within the 12-hour period between recharging events. Discernable radiation damage and changes to the diffraction pattern were observable in the samples used in Example 1 and Example 2 after about 36 hours in the beam line after when working with 0.7 Å radiation.

In the preferred embodiment of the invention, data are collected at the temperature that minimizes the line width of the peaks measured in the diffraction experiment. In the examples shown, room temperature is preferred. However, in situations where a longer lifetime in the beam is desired, the diffraction step may be performed at lower temperatures using cryoprotectants and cooling protocols if necessary or desired.

In another preferred embodiment of the invention the sample is rotated during the collection of data. This can help to ensure good powder averaging, for example as described in Chapter 9 of the book by R. Jenkins and R. L. Snyder *Introduction to X-ray Powder Diffractometry*, John Wiley & Sons, Inc. (1996).

Referring also to Example 3, neutrons may also provide a radiation source for diffraction data. Neutrons for diffraction experiments may be produced from nuclear reactors fueled by $^{235}$U or $^{239}$Pu and may be used to perform diffraction experiments at constant wavelength. Neutrons may also be generated by a spallation source in which a high-energy beam of protons produced by an accelerator is allowed to strike a heavy metal target. The accelerator may be operated in pulse mode resulting in a narrow, polychromatic, pulse of neutrons, which enables time of flight energy analysis to be employed in the interpretation of the diffraction pattern. Neutron sources for powder diffraction experiments are described in more detail by R. B. Von Dreele, *Neutron Powder Diffraction*, Chapter 11 of *Modern Powder Diffraction*, Reviews in Mineralogy Volume 20, Edited by D. L. Bish and J. E. Post (1989).

The mechanism of scattering in X-ray and neutron diffraction experiments is different and therefore the probed scattering density, $\rho(r)$, is different. X-ray scattering occurs by interaction of the X-rays with the electrons of the material and as a result there is a wide range in the X-ray scattering power of atoms and scattering power increases from the top to the bottom of the periodic table. Neutrons are scattered by the nuclei of the material and the scattering power may be expressed in terms of a neutron scattering length. In contrast to X-rays, the neutron scattering power of an atom is isotope dependent and, to within a factor of about two or three, most atoms elastically scatter neutrons equally well. The neutron scattering power is the sum of two terms, the coherent and incoherent cross section. Coherent scattering gives rise to diffraction, while incoherent scattering serves only to increase the background in the diffraction pattern.

The information that may be derived from X-ray and neutron diffraction experiments is complementary, as a consequence of the different scattering properties of each atom with these methods. In some applications, a combination of X-ray and neutron data may prove useful with the powder diffraction method as has been shown in the study of some inorganic materials.

In X-ray diffraction experiments hydrogen, with just one electron, is the atom with the weakest scattering power and is therefore the element that is most difficult to observe in an X-ray diffraction pattern. Neutrons however are strongly scattered by both hydrogen and deuterium and are therefore much more amenable to study with neutron diffraction experiments. Hydrogen frequently accounts for about one-half of the total number of atoms in a macromolecule and is both functionally and structurally important. The neutron scattering lengths of hydrogen and deuterium are of opposite sign and the contrast of parts of a crystal structure under study, such as the solvent molecules, may be usefully varied by adjusting the ratio of deuterium to hydrogen in that part of the structure. It should also be noted that in the case of biologically relevant nuclei the coherent cross section accounts for approximately 75-100% of the total cross section, with the exception of hydrogen where the ratio is only 2%. Neutron scattering experiments on fully hydrogenated macromolecular systems is usually dominated by a large incoherent background and it may be desirable to replace some or all of the hydrogen with deuterium to improve the signal to noise ratio in the experiment. Application of single crystal neutron diffraction to macromolecules is discussed by Z. R. Korszun in *Neutron Macromolecular Crystallography*, Methods in Enzymology, 276, 218-232 (1997).

Accordingly, it will be understood that different types of radiation, diffractometers and data may be used individually or collectively and remain within the methods of the invention as disclosed and claimed herein.

Referring now to block 26 of FIG. 2, once the diffraction data of the unbound macromolecule and the macromolecule-ligand complex are collected it is preferred that the diffraction pattern of the macromolecule-ligand complex be generally compared to the diffraction pattern of the unbound macromolecule to determine whether there are significant differences between the two diffraction patterns. It is understood that significant differences means differences that are greater than would normally be observed between two diffraction patterns measured on nominally identical macromolecule samples. Differences may be caused by variations of equipment over time and the fact that the measurement of diffraction intensity at each Bragg angle will vary between different experiments as a consequence of finite counting statistics. The absence of significant differences between the two patterns may be an indication that the macromolecule-ligand complex did not form during the sample preparation step. Many factors may contribute to the formation of a macromolecule ligand complex. For example if the macromolecule-ligand sample was formed by co-crystallization, the macromolecule-ligand complex may fail to form in significant concentration in solution if the macromolecule-ligand complex has a large dissociation constant.

If no significant differences are observed in the diffraction in a preferred embodiment of the invention microcrystalline samples of the macromolecule and macromolecule-ligand complex will normally be remade at block 30 of FIG. 2. Block 30 may include repeating all of the steps previously outlined in blocks 20 and 22. The goal of remaking the samples in block 30 is to use alternative conditions that will encourage the formation of the macromolecule-ligand complex in the microcrystalline macromolecule-ligand complex sample. Many factors may be varied to promote the formation of the complex such as changing the temperature, pH, choice of solvents and the choice and concentration of reagents used in sample preparation.

If it is established that significant differences exist between the diffraction patterns of the samples of the unbound macromolecule and the macromolecule-ligand complex, in block 26, in a preferred embodiment of the invention analysis may proceed to block 28 of FIG. 2. In block 28, the diffraction patterns on the unbound macromolecule and the macromolecule-ligand complex samples are analyzed to establish whether the microcrystals may be isostructural. It will be understood that the microcrystalline material in the two samples may be considered to be isostructural if they have crystallized in the same space group and that lattice parameters differ by only a few percent. A signature of the fact that the macromolecules in the two samples are isostructural is that the peak positions and peak intensities in the two diffraction patterns vary by approximately a few percent. For example, intensity changes of approximately 1% to approximately 10% may be observed with a 10-100 atom ligand bound to a 1000 atom protein. One can estimate this from $$[\Sigma f_i^2(\text{bound}) - \Sigma f_i^2(\text{unbound})]/\Sigma f_i^2(\text{unbound})$$

where $f_i(\text{bound})$ and $f_i(\text{unbound})$ are the atomic numbers of the non-hydrogen atoms of the macromolecule and the macromolecule ligand complex respectively and the sum over i runs over all non hydrogen atoms in the structure. For a typical non-hydrogen atom in a macromolecule and an organic ligand $f_i \sim 7$.

In a preferred embodiment of the invention, if it is found that isostructural samples were not produced at block 28 of FIG. 2, it should be determined whether to remake samples at block 30 of FIG. 2, or whether to proceed with an alternative analysis BB, shown in more detail in FIG. 4. Several factors may influence the decision making process. The preferred data analysis steps beginning with AA of FIG. 3, which requires that the samples of the unbound macromolecule and macromolecule-ligand complex to be isostructural, are often simpler to accomplish than the data analysis steps beginning with BB of FIG. 4. Therefore data analysis considerations tend to favor remaking samples at block 30 of FIG. 2 to attempt to obtain isostructural microcrystalline material. However, if several attempts at sample preparation have failed to produce isostructural samples, data analysis via the steps beginning with BB in FIG. 4 may become the favored next step because isostructural samples are not required with these steps and remaking the samples is not a practical solution.

Other factors may weigh in favor of using the alternative data analysis steps beginning with BB in FIG. 4. For example, high costs or low availability of the macromolecule, ligand or other reagents needed for sample preparation may favor the alternative analysis. Likewise, the high cost and/or low availability of experimental facilities to perform diffraction measurements may favor the alternative analysis. Accordingly it will be seen that the outcome of the decision making process at block 32 may be influenced by the macromolecule and ligand under study and the facilities available to those practicing the invention.

Referring still to block 32 of FIG. 2, if it is determined that it is practical to remake microcrystalline samples of the macromolecule or macromolecule-ligand complex, the samples are remade at block 30 of FIG. 2. Samples may be remade according to one of the methods outlined previously in blocks 20 and 22 of FIG. 2, using different preparation conditions to encourage the formation of isostructural samples. Many factors may be varied to promote the formation of the complex such as changing the temperature, pH, choice of solvents and choice and concentration of reagents used in sample preparation. Alternatively, as noted previously, formation of an isostructural sample of the macromolecule-ligand complex may also be undertaken by soaking a microcrystalline sample of the unbound macromolecule in a solution containing the ligand.

Referring now to FIG. 3, once the binding of the ligand to the macromolecule and suitability of the diffraction data has been confirmed, the analysis of the diffraction data is preferably conducted using the steps beginning with block 34 in the embodiment shown. In a preferred mode of the invention an approximate crystal model for the unbound macromolecule is first obtained. At question block 34, of FIG. 3, it is determined whether a single crystal structure or other crystal model of the unbound macromolecule is already available which is isostructural with the macromolecules in the microcrystalline samples to be analyzed. This may be achieved, for example, by first generating a list of known crystal structures that contain the macromolecule by searching a database of macromolecule structures such as the publicly available Protein Data Bank. See H. M. Berman, J. Westbrook, Z. Feng, G. Gilliland, T. N. Bhat, H. Weissig, I. N. Shindyalov, P. E. Bourne: *The Protein Data Bank.* Nucleic Acids Research, 28 pp. 235-242 (2000). In one embodiment, a Rietveld refinement using the structures of any of the single crystal structures identified in this process may then be performed against the powder diffraction pattern of the unbound macromolecule to determine whether the macromolecules in the single crystal structure and the microcrystalline samples are isostructural. In some cases the formula unit of a single crystal macromolecule structure may contain additional atoms or additional structural elements, such as bound ligands that are absent in the microcrystalline sample of the unbound macromolecule. It is preferred that such additional atoms or structural elements should be deleted from the single crystal model before beginning the process of refinement such as a Rietveld refinement. Typically, the Rietveld refinement may involve optimizing the background parameters including the scale factor, the lattice parameters and the peak profile parameters, while the atom positions of the macromolecule are held fixed. The solvent parameters may also be refined. If the macromolecules in the single crystal study and the microcrystalline sample are isostructural, the lattice parameters should change by no more than a few tenths of a percent in the course of a Rietveld refinement. In addition, the peak positions and peak intensities in the refined profile should match those of diffraction pattern of the unbound macromolecule to within a few percent and a few tenths of a percent, respectively. It will be appreciated that many variations of the above method for determining whether the macromolecule in the single crystal and unbound macromolecule sample are isostructural may be used, while remaining within the scope of the current invention. It will be understood that there is flexibility with regard to the choice of parameters that are optimized in a Rietveld refinement. It is also understood that the refinement process, in which the differences between the observed and calculated diffraction patterns are minimized, may deviate from the standard Rietveld method. For example, the standard least squares optimization of the Rietveld method for minimizing the objective function in the Rietveld method may be replaced with other kinds of minimizers, such as those based on conjugate gradient methods.

There are some cases where it may be possible to completely avoid the Rietveld refinement process, by instead utilizing a set of observed integrated structure factor sums extracted from the powder diffraction pattern. See for example H. Toraya, *Position-Constrained and Unconstrained Powder-Pattern-Decomposition Methods*, in Chapter 14 of *The Rietveld Method*, Edited by R. A. Young, Oxford University Press 1993. The observed structure factor sums may then be correlated with calculated or measured structure factors of the single crystal model. Space group and lattice parameter similarity is a good indication that the materials are isostructural. A strong correlation between the structure factors is also an indication that the materials are isostructural.

If an isostructural single crystal diffraction model for the microcrystalline sample of the unbound macromolecule is found to be available in block 34 of FIG. 3, in a preferred embodiment of the invention, an approximate unbound macromolecule crystal model is then derived in block 36 of FIG. 3. The approximate unbound macromolecule crystal model may, for example, be taken as the final structure derived from the Rietveld refinement step of block 34 on the isostructural single crystal model.

If an isostructural single crystal diffraction model for the microcrystalline sample of the unbound macromolecule can not be identified in block 34 of FIG. 3, preferably an approximate unbound macromolecule crystal model may be derived by analysis of the powder diffraction pattern of the unbound macromolecule in blocks 40, 42 and 44 of FIG. 3.

Turning first to block 40 of FIG. 2, possible lattice parameters and possible space groups of the crystal may be determined. The technique of indexing may be applied to index peaks in the diffraction pattern with h, k, and l values, and to infer likely values of the lattice parameters, given an accurate list of d-spacings. An accurate list of d-spacings may be obtained, for example, by peak fitting of individual reflections of the diffraction pattern of the unbound macromolecule. Indexing of powder diffraction patterns may be performed with the assistance of software such as ITO, TREOR and DICVOL and the like. For each likely choice of lattice parameters the crystal class and possible space groups of the crystal may be determined through an analysis of systematic absences of diffraction peaks in the powder diffraction pattern. See R. B. Von Dreele, P. W. Stephens, G. D. Schmidt and R. H. Blessing, *The First Protein Crystal Structure Determined from High-resolution X-ray Powder Diffraction Data: A Variant of $T_3R_3$ Human Insulin-Zinc Complex Produced by Grinding*, Acta Cryst. D56, 1549 (2000). Natural macromolecules, such as proteins and DNA, contain chiral centers and as a consequence can crystallize in only 65 out of the 230 possible space groups, simplifying the assignment of space groups.

Turning now to block 42 of FIG. 3, in the next step a molecular model of the macromolecule that is the subject of the investigation is preferably provided. The molecular model of the macromolecule may be derived, for example, from a prior structure obtained using experimental techniques such as solution NMR or single crystal X-ray diffraction. An online public domain database of macromolecular structures, the Protein Data Bank may also provide a source for a model. The molecular model of the macromolecule may also be derived using methods for protein structure prediction such as comparative or homology modeling, fold recognition or ab initio prediction. For example, various protein structure prediction methods are described by Moult et al. J. Moult, T.

Hubbard, K Fidelis, J. T. Pedersen, *Critical Assessment of Methods of Protein Structure Prediction (CASP): Round III*, PROTEINS: Structure Function and Genetics Suppl. 3:2-6 (1999).

In block 44 of FIG. 3 an approximate unbound macromolecule crystallographic model is derived in a preferred embodiment of the invention. An estimated density of the crystal macromolecule may be combined with lattice parameter and space group information to infer the number of macromolecules in the asymmetric unit cell of the crystal, and may be beneficially used to estimate whether special positions in the unit cell are occupied. In one embodiment of the invention, an ensemble of possible approximate unbound macromolecule crystal models is considered. The ensemble of models may be generated by rigidly placing the molecular model of the macromolecule obtained in block 42 into the one or more likely unit cells identified in block 40 with different choices of origins and orientations using different possible space groups identified in block 40. Methods for generating the series of choices of origins and orientations in the ensemble include, but are not limited to, exhaustive searches on grids, Monte Carlo methods, genetic algorithm based methods as well as rigid body Rietveld refinements of the macromolecule coordinates against the powder diffraction data and methods that combine these approaches. The process may be further assisted by the use of scoring functions that measure the extent to which each member of the ensemble fits observed data and known properties of macromolecular systems. The scoring may be designed such that probable arrangements of the macromolecule result in low values while improbable arrangements result in high values. A possible choice of scoring function is one of the Rietveld numerical criteria of fit such as $R_F$, $R_p$ or $R_{wp}$, calculated by performing a Rietveld refinement in which profile, scale factors and background parameters are optimized for each member of the ensemble. The scoring function may also be designed so that its value grows as the overlaps between macromolecules in the system grow. It may further also incorporate information based on evaluation of the energy of the arrangement of the macromolecules computed using force field or other methods. The scoring function may be used, for example, to generate new conformations of the macromolecule in a Monte Carlo simulated annealing approach to identify the origin and orientation of the macromolecule. See, for example, G. E. Engel, S. Wilke, O König, K. D. M. Harris and F. J. J. Leusen, *Powder Solve—A Complete Package for Crystal Structure Determination from Powder Diffraction Patterns*, J. Appl. Cryst. 32, 1169-1179 (1999). In a preferred embodiment of the invention the approximate unbound macromolecule crystal model is taken to be that member of the ensemble that minimizes the scoring function.

If one or more aspects of the approximate crystallographic model of the unbound macromolecule derived at block 44 are unsatisfactory, for example because the model with the best R values has substantial overlap between adjacent macromolecules, it is understood that one or more alternative molecular models of the macromolecule may be derived using the methods described at block 42 and the methods of block 44 reapplied with the one or more alternative molecular models in an effort to derive a satisfactory approximate crystallographic model of the unbound macromolecule.

It is also understood that in some cases it may be possible to provide high quality molecular models of one or more fragments of the macromolecule at block 42, but that a high quality model of the entire unbound macromolecule may be unavailable. In such cases it is preferred that the search methods described in block 44 are applied to the individual fragments in an effort to generate an approximate crystallographic model for the unbound macromolecule. For example, an ensemble of crystallographic models may be generated by rigidly placing the molecular models of the one or more fragments in the likely unit cells derived at indexing block 40. The models may be generated using, for example, using Monte Carlo methods, grid based search methods, or rigid body Rietveld refinement. Scoring functions, as described previously, may be used to select a superior approximate crystallographic model of the unbound macromolecule for further analysis. If there are sections of the macromolecule that are not described by any of the one or more fragments the technique of structure completion may be utilized in an effort to place the missing parts of the macromolecule. For example, a scattering density map, such as a difference Fourier map, may be used to infer the positions of missing parts of the structure and those missing parts of the structure placed into the crystallographic model using computer based molecular visualization software.

Accordingly, there are several ways to derive an approximate model for the unbound macromolecule that provides the approximate parameters of the macromolecule in the unit cell at block 44 of FIG. 3.

Turning now to the step shown at block 38 of FIG. 3, a refined crystal structure for the unbound macromolecule is then obtained by refining the approximate model for the crystal structure against the powder diffraction data using a combined Rietveld and stereochemical restraint refinement in the embodiment shown. See generally, R. B. Von Dreele, *Combined Rietveld and Stereochemical Restraint Refinement of a Protein Crystal Structure*, J. Appl. Cryst. 32, 1084 (1999).

The addition of stereochemical restraints to the refinement process is normally necessary because the number of Bragg peaks in the useful range of the diffraction data is typically less than the number of positional parameters to be refined. Stereochemical restraints augment the information available in the diffraction data by restraining variables such as bond lengths, bond angles and torsions in the macromolecule or the macromolecule-ligand complex to conform to chemically reasonable values.

It is preferred that the structure is checked after every few cycles of Rietveld refinement to ensure that the geometry of the structure is stereochemically reasonable.

For example, in the setting where the macromolecule is a protein, the program PROCHECK or similar program can be used to assess the overall quality of the structure. See R. A. Laskowski, M. W. MacArthur, D. S. Moss, and J. M. Thornton, *PROCHECK: A Program to Check the Stereochemical Quality of Protein Structures*, J. Appl. Cryst. 26, 283-291 (1993). If certain parts of the macromolecule are observed to deviate strongly from statistically likely values, the molecular geometry of the macromolecule may be changed to locate a more statistically usual conformation. In the case of proteins, such changes may be conveniently effected, for example, by using the "mutate" tool of the Swiss PDBViewer, which enables the conformation of particular residues to be adjusted interactively using computer graphic models of the protein. N. Guex and M. C. Peitsch, *SWISS-MODEL and the Swiss-PdbViewer: An environment for comparative protein modeling*, Electrophoresis 18, 2714-2723 (1997). These changes can also be guided by the use of difference Fourier maps or OMIT maps.

In addition, the combined Rietveld and stereochemical restraint refinement may be assisted by intermediate force field energy minimizations via, for example, the GROMOS force fields. W. F. van Gunsteren et al. in *Biomolecular simulation: the GROMOS96 manual and user guide*, Verlag der Fachvereine, Zürich, pp 1-1024 (1996). In a preferred embodiment of the invention, the combined Rietveld and stereochemical restraint refinement is converged and a single cycle of force field energy minimization performed. The combined Rietveld and stereochemical restraint refinement may then be applied a second time to the resulting structure until the refinement converges.

It will be understood that many variations of the refinement process at block 38 may be possible, while still remaining within the scope of the invention. For example, the minimization process in the refinement process need not use the least-squares minimization techniques usually employed in the Rietveld method and such techniques may be replaced by other minimization techniques such as those based on conjugate gradient minimization and the like. In another embodiment of the invention, the refinement may be conducted by, or assisted by, extracting a set of observed integrated structure factor sums from the powder diffraction pattern and performing a refinement of the approximate structure of the macromolecule refined against the integrated structure factor sums.

To facilitate processing of the diffraction data computer programs are preferably used. For example, the GSAS program is a freely available package that runs on a number of different computer platforms and contains facilities for performing Rietveld refinement of powder diffraction data. Larson, A. C. & Von Dreele, R. B. (2001). *General Structure Analysis System (GSAS)*, Los Alamos National Laboratory Report LAUR 86-748. The standard distribution of GSAS includes capabilities for applying stereochemical restraints. GSAS also includes capabilities for performing calculations with rigid body constraints and for computing various Fourier maps.

In the next step of a preferred embodiment of the invention, at block 46 of FIG. 3, a difference Fourier map for the macromolecule-ligand complex is then developed using the refined coordinates of the unbound macromolecule to approximate the positions of the atoms of the macromolecule in the macromolecule-ligand complex. While a difference Fourier map is preferred, it will be understood that other scattering density maps and methods may be utilized. Prior to generating the difference map, it is preferred that the diffraction pattern of the macromolecule-ligand sample be "fitted" so as to obtain optimal values of the lattice parameters, profile coefficients, scale factors and to fit the background of the powder diffraction pattern. It is also preferred that the fractional coordinates of the macromolecule are held fixed in the refinement. Calculation of the difference Fourier map entails combining the calculated structure factor amplitudes and phases for the unbound macromolecule with structure factor amplitudes extracted from the powder diffraction pattern of the macromolecule-ligand complex. This extraction process may be accomplished during a Rietveld refinement by apportioning the observed diffraction profile above background among the contributing reflections according to the ratio of their calculated intensities. In this way, a set of integrated intensities are obtained for all reflections within the range of the powder profile; they are then subjected to the usual corrections for reflection multiplicity, Lorentz and polarization to obtain a set of "observed" structure factors.

In an alternative embodiment, the scattering density map may be improved by weighting various structure factors. For example, contrast in a difference map may be achieved through the Sim weighting option the GSAS program. Sim, G. A. (1960) Acta Cryst. 13, 511-512. Likewise, the scattering density maps may also be provided using maximum entropy principles such as through the use of a maximum entropy reconstruction. For example see, Kumazawa et al. (1993) J. Appl. Cryst. 26, 453-457. Such maps tend to have less background noise than Fourier maps and may therefore show features more clearly. In a preferred mode of the invention, the binding site of the ligand is then determined by an analysis of the difference Fourier map to locate the ligand-density volume at block 46 of FIG. 3. A preferred method for analyzing the difference Fourier map is to use computer graphics to simultaneously visualize the macromolecule and the difference Fourier map. For example the geometry of the macromolecule may be displayed using a ball and stick model to represent the atoms and bonds in the macromolecule while the isosurface maps may be used to display the difference Fourier map. Such visualization may be achieved in practice, for example, by first using the GSAS program, cited above, to write out the coordinates of the macromolecule in pdb format and the difference Fourier map in dn6 format. The macromolecule coordinates and difference Fourier map may then be read into the Swiss PDBViewer software, cited above, in these formats for interactive visualization. The ligand is a missing piece of the model for the macromolecule-ligand complex used to generate the difference Fourier map and its presence in the structure will often give rise to the ligand-density volume, a large contiguous region of high density in the difference Fourier map. An especially preferred technique for locating the ligand-density volume is to visually identify that isosurface that contains the largest volume of space when the difference Fourier map is displayed with a isosurface contour in the approximate range of 1.0-1.5 standard deviations of the difference density distribution in the map. The Swiss PDBViewer has other capabilities that aid in the inspection of the difference Fourier map including the ability to limit the display of the map to defined regions of space and the ability to view models in stereo. It is also possible to use automatic computer search methods to detect the binding site of the ligand based on Fourier maps. See for example T. J. Oldfield, *X-LIGAND: an application for the automated addition of flexible ligands into electron density*, Acta Crystallogr. D57 696-705 (2001).

Turning now to block 48 of FIG. 3, in a preferred embodiment, an approximate macromolecule-ligand crystal model is generated. This may be accomplished by docking a three-dimensional model of the ligand into the previously identified ligand-density volume and allowing the fit of the ligand to be optimized by making low energy distortions of the ligand.

In a preferred embodiment of the invention an appropriate three-dimensional model of the ligand may be produced by making a two dimensional sketch of the structure of the ligand in a molecular modeling software package. The two to three dimensional conversion utilities of such packages may then be applied to obtain a three-dimensional model of the ligand. An example of a package that provides such capabilities is the WebLab ViewerPro product marketed by Accelrys Inc. of San Diego Calif. The three dimensional model of the ligand may also be obtained from other sources such as experimental databases of molecular structures or from more sophisticated computer simulations based on force field or quantum mechanical methods.

In a preferred embodiment of the invention, the docking of the three dimensional model of the ligand may be performed manually with the use of computer graphics and software. For example software packages are available that enable the simultaneous display of the difference Fourier map, the three-dimensional model of the ligand and that also include interactive capabilities for manipulating the position, orientation and internal coordinates of the three-dimensional model of the ligand. An example of a software package with such capabilities is the Swiss PDBViewer. The docking of the ligand may also be accomplished automatically by computational methods. See for example T. J. Oldfield, *X-LIGAND: an application for the automated addition of flexible ligands into electron density*, Acta Crystallogr D57 696-705 (2001). If the difference Fourier map does not contain sufficient detail to place the whole ligand, a fragment of the ligand or one or more heavy atoms may be placed into the binding site and the structure refined using combined Rietveld and stereochemical restraint refinement. The map may then be regenerated with the updated estimates of structure factor amplitudes and phases to see whether additional detail regarding the ligand position is available and the process is iterated until it becomes possible to place the entire ligand into the map.

The analysis is continued, if necessary, by performing a Rietveld and stereochemical restraint refinement on the approximate macromolecule-ligand model that was generated from the difference Fourier map as seen at block 50 of FIG. 3, for example. A combined Rietveld stereochemical-restraint refinement may then be performed against the diffraction pattern of the model for the macromolecule-ligand complex to obtain optimized positions of atoms in the complex, using the procedures that were described previously for the case of the unbound macromolecule.

The results of the analysis are interpreted at the step at block 52. With the production of the refined macromolecule-ligand crystal model in the previous step, the identity of the amino acid side chains of the macromolecule involved in the active site or sites of the molecule as well as the atoms of the ligand interacting with the active site and other useful information can be identified. For example, the binding mode of the ligand can be compared with the binding modes of other ligands. Such comparisons may disclose the full range of possible interactions between a family of ligands and a particular active site on the macromolecule. Accordingly, the interaction of progressively modified ligands with the active sites of the macromolecule can be compared and can act as a guide to further modifications of the ligand to enhance a biological or pharmacological property of the ligand. Likewise, the enhanced binding of a new modified ligand in the binding site, for example, can be demonstrated by the successive comparisons of modified ligands. Furthermore, the biological or pharmacological effect of the modified ligands can be investigated with binding assays, in vivo trials and the like and then correlated with similar studies for the natural ligand and other modified ligands in the scheme. In addition, comparisons of the modes of interaction may provide guidance for providing progressively modified antagonists to the natural ligand and the biological activity of such antagonists can be confirmed by subsequent experimentation or compared and correlated with existing experimental data.

Referring now to FIG. 4, an alternative method of analysis is provided when isostructural samples of the macromolecule or macromolecule-ligand complex is not practical as determined in question block 32 of FIG. 2. The analysis method of FIG. 4 enables the structure of the macromolecule-ligand complex to be obtained when the macromolecules in the unbound macromolecule and macromolecule-ligand samples are not isostructural.

The objective of steps at block 54 through 60 and 64 of the first section of the analysis depicted in FIG. 4 is to obtain a refined crystallographic model of the unbound macromolecule at block 62 of FIG. 4. In a preferred embodiment of the invention the steps 54, 56, 58, 60, 62 and 64 involved in obtaining the refined unbound macromolecule crystallographic model are essentially the same as the previously described steps 34, 36, 38, 40, 42 and 44, used to accomplish this process in the flow diagram in FIG. 3. Accordingly, at block 56, the diffraction data of the unbound macromolecule is preferably indexed to obtain cell parameters and possible space groups etc.

A molecular model of the unbound macromolecule is preferably provided at block 58, of FIG. 4. The molecular model may be obtained through homology modeling, ab initio folding, threading, NMR or single crystal X-ray diffraction or the like. In one embodiment, several molecular models are provided when there is uncertainty about the selection of the best model. In this embodiment, each of the molecular models of the group of models is tried and then the molecular model that provides the best explanation of the unbound macromolecule diffraction data is selected and then used to derive the approximate unbound macromolecule model in block 60.

At block 60 of FIG. 4 the approximate model of the unbound macromolecule is obtained using the molecular model and the diffraction data from the unbound macromolecule to place the macromolecule in the unit cell. There are several ways that the approximate crystallographic model of the unbound macromolecule can be developed including the use of Monte Carlo techniques for placing a molecule in a unit cell, grid searches and rigid body Rietveld refinement. Optionally, the placement process can be assisted by accounting for other factors such as the experimental and theoretical density of the system, the overlap between the macromolecules, force energy calculations to assess reasonableness of the packing arrangement and analysis of whether there are favorable contacts between the surfaces of the macromolecule. Alternatively, when a single crystal model of the unbound macromolecule is available then that model may serve as the approximate crystallographic model of the unbound macromolecule as provided in block 64.

In the embodiment shown, a combined Rietveld and stereochemical restraint refinement is conducted on the approximate model of the unbound macromolecule to provide a refined unbound macromolecule crystallographic model in block 62 of FIG. 4.

Turning now to block 66 of FIG. 4, once the refined unbound macromolecule crystallographic model has been derived at block 62, the diffraction pattern of the macromolecule-ligand complex is may then be indexed to obtain likely lattice parameters and possible space groups of the crystal of the complex. The procedures and methods that may be used to index the patterns are the same as those described previously in block 40 of FIG. 3, except that here they are applied to the diffraction pattern of the macromolecule-ligand complex, rather than the diffraction pattern of the unbound macromolecule.

An approximate model of the crystal structure of the macromolecule-ligand complex, in the absence of the ligand, may be obtained in the step at block 68 of FIG. 4, once lattice parameters and possible space groups have been identified. The structure of the unbound macromolecule derived in block 62 may be used to obtain approximate macromolecule-ligand crystallographic model in the absence of the ligand. In one embodiment of this process, an ensemble of possible approximate crystal structures may be generated by rigidly placing the structure of the unbound macromolecule obtained in the step at block 62 into the likely unit cell provided in the step in block 66 to provide a series of choices of origin and orientation and space groups identified in the step at block 66. The structures may be generated, and an optimal structure selected, using the methods described previously in block 44 of FIG. 3.

Once an approximate macromolecule-ligand crystallographic model, without the ligand, has been identified in block 68, analysis may proceed to the calculation of a difference Fourier map in block 70 of FIG. 4 in the embodiment shown. In a preferred embodiment of the invention, a Rietveld refinement of the approximate macromolecule-ligand crystal model without the ligand is performed against the macromolecule-ligand diffraction pattern to optimize the lattice parameters, profile coefficients, scale factors and to fit the background of the powder pattern. It is preferred that the fractional coordinates of the macromolecule are not adjusted in the course of the refinement process. A difference Fourier map may then be calculated using the resulting crystal structure. Although a difference Fourier map is preferred, it is not essential. It will be understood that other maps and techniques may be used to determine the location of the ligand and the macromolecule structure that are known in the art as described herein.

In a preferred embodiment of the invention, analysis may be continued in the steps depicted in blocks 72, 74 and 76. These steps precisely parallel those described previously in blocks 48, 50 and 52 in FIG. 3. Accordingly, an approximate macromolecule-ligand crystallographic model is derived at the step at block 72. Preferably, a combined Rietvelt and stereochemical restraint refinement is conducted on the approximate macromolecule-ligand crystallographic model derived at block 72 to provide a refined macromolecule-ligand crystallographic model derived at block 74. The results are interpreted at block 76 as previously described at block 52 of FIG. 3.

Figure 5:
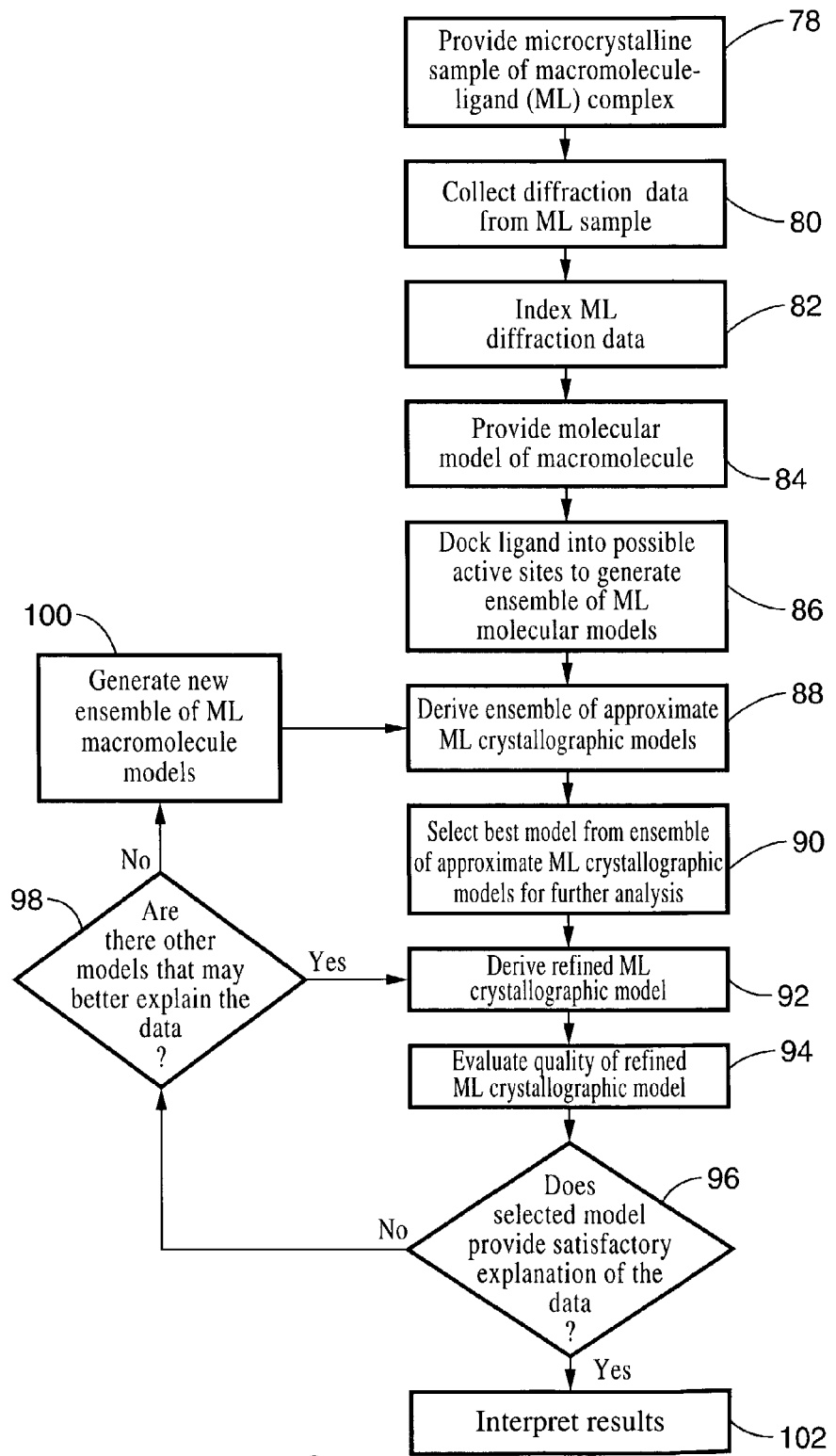
FIG. 5 is a flowchart of an alternative embodiment of the analysis and results interpretation substeps according to one aspect of the present invention.
Figure 6:
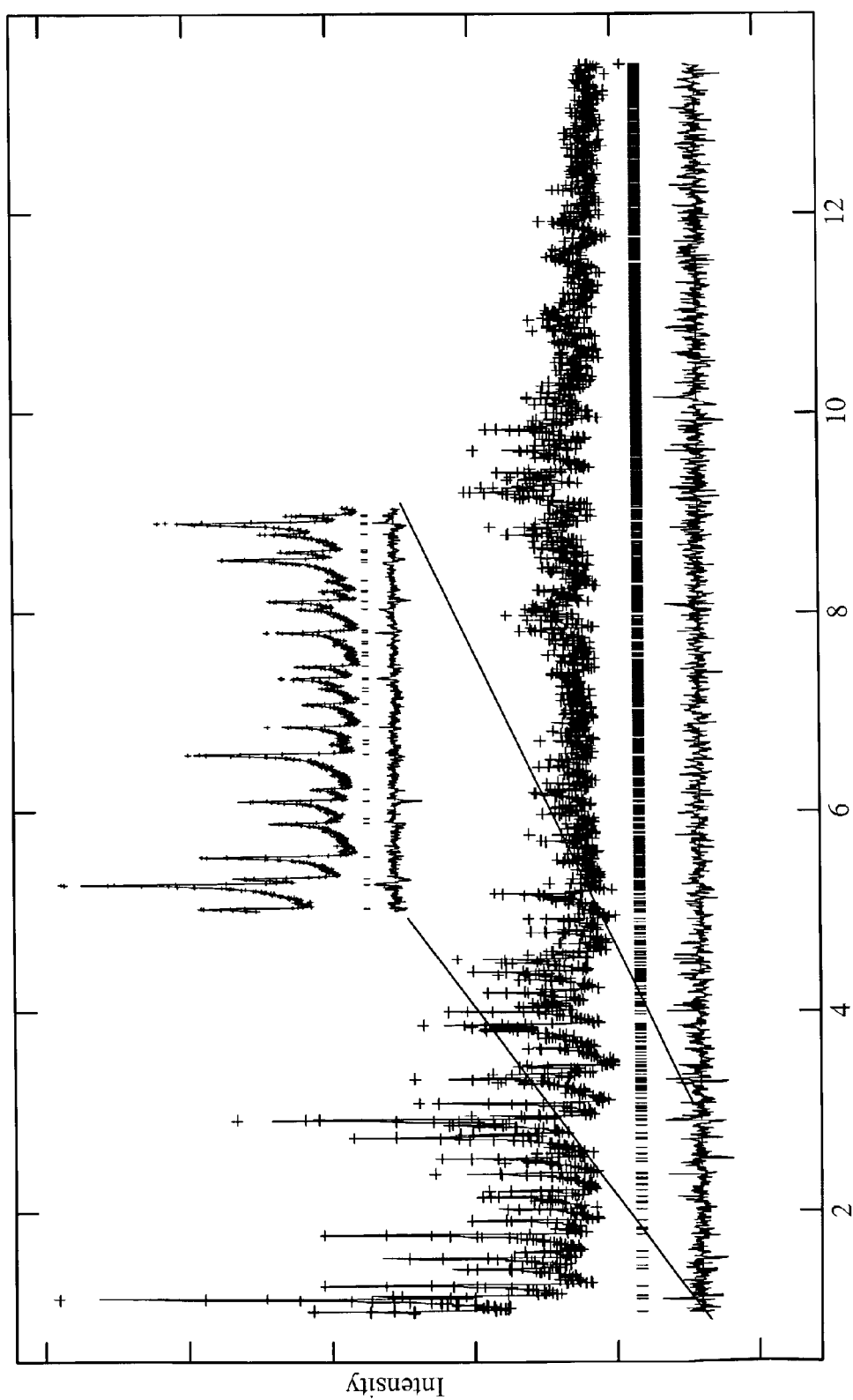
FIG. 6 is a high resolution X-ray powder diffraction profile of the lysozyme-NAG complex according to one aspect of the present invention resulting from the final combined Rietveld stereochemical refinement.

Turning now to FIG. 5, an alternative set of analysis steps of the diffraction data is shown. In this embodiment, a docking approach to analyzing the structure of macromolecule-ligand complexes is provided. Unlike the previously described embodiment, diffraction patterns from the unbound macromolecule are not required.

The analysis of the macromolecule-ligand complex may begin at block 78 by providing a suitable microcrystalline powder of the macromolecule-ligand complex. Microcrystalline powders of the macromolecule-ligand complex may be made using the methods described previously at block 22 of FIG. 2. A preferred method of creating microcrystals is through the crystallization of lyophilized macromolecules as described herein.

Diffraction data of the macromolecule-ligand complex are then collected at block 80, using for example X-ray, neutron or electron sources as described previously at block 24 of FIG. 2. In a preferred embodiment of the invention the diffraction pattern is measured using X-ray radiation generated at a synchrotron source.

Moving now to block 82 of FIG. 5, in a preferred embodiment of the invention the diffraction pattern measured at block 80 is indexed and likely lattice parameters and possible space groups of the macromolecule-ligand crystal structure determined. Methods that may be used to index the diffraction data have been previously described in connection with block 40 of FIG. 3.

At block 84 of FIG. 5 in a preferred embodiment of the invention a molecular model of the macromolecule is provided. Methods that may be used to provide a suitable molecular model of the macromolecule have been previously described at block 42 of FIG. 3.

At block 86 of FIG. 5, in a preferred embodiment of the invention, an ensemble of macromolecule-ligand molecular models may be generated by docking models of the ligand into possible binding sites on the macromolecule. Generation of the ensemble may be initiated, for example, by the identification of possible ligand binding sites on the macromolecule. Ligands, such as drug molecules, often bind into clefts or pockets of their target macromolecule, which is frequently the active site of an enzyme or a binding site of a receptor. In such cases it may be possible to identify possible binding sites by visual inspection of the macromolecule, using for example, computer graphics. In addition, the identification of binding sites may be assisted by the use of experimental information such as previously determined ligand-binding sites of related macromolecules. Putative binding sites may also be identified by automated methods. See R. T. Kroemer *Molecular Modeling* in Chapter 2 of *Protein-Ligand Interactions: Structure and Spectroscopy*, edited by S. E. Harding and B. Z. Chowdhry, Oxford University Press (2001). In a preferred embodiment of the invention, a three dimensional structure of the ligand is then provided and the ligand docked into the previously identified binding sites. It is preferred that the flexibility of the ligand is considered in the docking process, by for example, performing the docking steps with an ensemble of low energy conformers of the ligand. The docking of the ligand into the putative binding sites may be accomplished by hand, for example, with the assistance of suitable software and computer graphics. In a preferred embodiment of the invention automated docking programs are used to generate possible macromolecule-ligand structures. Such programs may, for example, perform grid searches to fit the conformers of the ligand into the putative binding sites by rotating and translating the ligand in discrete steps. Docking programs are also able to provide large numbers of possible macromolecule-ligand structures and in a preferred embodiment of the invention the quality of the resulting structures are ranked with a scoring function. The scoring function may, for example, evaluate an approximate free energy of each generated macromolecule-ligand complex using a force field or a force field augmented with terms to account for solvation, hydrophobicity or hydrogen bonding effects and the like. It is understood that the numerous alternative of approaches for macromolecule-ligand docking known in the art may be applied while remaining within the scope of the current invention. High quality structures resulting from the docking process, as measured by the scoring function for example, may then be used to generate the ensemble of macromolecule-ligand molecular models for further analysis.

Turning now to block 88 of FIG. 5 an ensemble of approximate macromolecule-ligand crystallographic models is generated. Preferably this process is initiated using the molecular macromolecule structure provided in block 84, the likely lattice parameters and possible space groups derived in block 82 and the diffraction pattern of the microcrystalline sample macromolecule-ligand complex obtained in block 80 to obtain the space group of the crystal and the approximate orientation and position of the unbound macromolecule in the unit cell. This may be accomplished for example using the methods previously described in relation to the steps at block 44 of FIG. 3. The ensemble of approximate macromolecule-ligand crystallographic models may then be generated by placing each member of the ensemble of macromolecule-ligand molecular models into the unit cell such that the coordinates of each macromolecule in the macromolecule-ligand complex are superposed with those previously identified for the unbound macromolecule.

Turning now to block 90 of FIG. 5, in a preferred embodiment of the invention, one member of the ensemble of approximate macromolecule-ligand crystallographic models is selected for further refinement. Several methods may be employed to select the model for refinement. For example, a Rietveld refinement in which background parameters, peak profile parameters and the scale factor is refined may be performed on each crystallographic model in the ensemble.

Numerical criteria of fit that are often used to assess the quality of Rietveld refinements such as R-structure factor ($R_F$), R-pattern ($R_p$) and R-weighted pattern ($R_{wp}$) may be computed for each resulting structure and a best structure selected on the basis of one or more of these fit criteria. There are many alternative combinations of parameters that may be selected for optimization in the Rietveld refinement. For example, rigid body optimizations may also be performed on the members of the ensemble before selecting a best model on the basis of a numerical criteria of fit. Other factors may also be included in the process of selecting a model including, for example, the overlaps between molecular entities in the crystal or the scoring function for each macromolecule-ligand molecular model computed previously in block 86.

Turning now to block 92 of FIG. 5, once a model has been selected for further analysis at block 90, the selected model is preferably subject to a further refinement to derive a refined macromolecule-ligand crystallographic model. In a preferred embodiment of the invention the refinement may be accomplished using a combined Rietveld-stereochemical restraint refinement using, for example, the methods described previously at blocks 38 and 50 of FIG. 3.

At block 94 the quality of the refined macromolecule-ligand crystallographic model derived in block 92 is evaluated. Many factors may be considered in assessing the model quality including the numerical criteria of fit obtained in the Rietveld refinement. If the macromolecule is a protein, the model quality may also be assessed, for example by examining the likelihood of the model using, the program PROCHECK, described above. Force field calculations may be used to verify that there are no bad contacts in the structure, for example, using the GROMOS force field discussed previously herein. The powder diffraction pattern of the macromolecule-ligand complex may also be used to further assess the quality of the model. For example, a further Rietveld refinement of the refined macromolecule-ligand crystallographic model may be performed in which the atoms of the ligand are divided into one or more groups and the site occupancies of each group refined, subject to the constraint that occupancies of all atoms in a group remain equal. Another use of the diffraction pattern to assess the quality of the model is through the calculation of Fourier maps. For example, an OMIT map may be computed in which the ligand, or part of the ligand, is omitted from the structure and the resulting map of the scattering density analyzed using computer graphics and suitable software. If the position of the ligand in the refined macromolecule-ligand crystallographic model is correct a volume of scattering density should be visible in the OMIT map for the omitted atoms. Alternatively, the OMIT map may indicate a possible improvement in the location of these atoms. At question block 96 of FIG. 5, the determination is made concerning whether the refined macromolecule-ligand crystallographic model provides a satisfactory explanation of the powder diffraction data and other factors that may have been considered in block 94. If it is determined that the refined macromolecule-ligand crystallographic model provides a satisfactory explanation of the data, analysis may proceed to block 102 of FIG. 5 where the results may be interpreted using, for example, the procedures outlined previously at block 52 of FIG. 3.

Conversely if it is determined that one or more aspects of the selected macromolecule-ligand crystallographic model do not provide a satisfactory explanation of the data, then a search may be conducted for a better model at block 98 of FIG. 5. At question block 98 of FIG. 5, the ensemble of approximate macromolecule-ligand crystallographic models may be further considered to assess whether any members of the ensemble may provide a better explanation of the data. For example, if there were several members of the ensemble of approximate macromolecule-ligand crystallographic models at block 90 whose potential to explain the data appeared comparable to the best model, one of these models may be selected and analyzed using the process described above beginning with the derivation of a refined macromolecule-ligand crystallographic model at block 92 of FIG. 5.

If no member of the ensemble of approximate macromolecule-ligand crystallographic models is found to be useful or desirable for further refinement and analysis, analysis may proceed to block 100 of FIG. 5 where a new ensemble of macromolecule-ligand models may be generated. The new ensemble may be generated at block 100 by using a more exhaustive search procedure or docking algorithms that may not have been previously considered at block 88. For example the range of possible binding sites considered may be expanded or a more exhaustive sampling method may be used to generate conformations of the molecular models of the macromolecule-ligand complex. The new ensemble may be screened to remove conformations of the macromolecule ligand complex that have been studied previously. The analysis described previously may then be applied to the ensemble of macromolecule-ligand molecular models starting at block 88 of FIG. 5 in an effort to derive a crystallographic model of the macromolecule-ligand complex that provides a satisfactory explanation of the data.

Once the structure of the macromolecule-ligand complex is satisfactorily explained, the results may be interpreted at block 102 as described in block 52 of FIG. 3.

The invention may be better understood with reference to the accompanying examples, which are intended for purposes of illustration only and should not be construed as in any sense limiting the scope of the present invention as defined in the claims appended hereto.

EXAMPLE 1

A sample of lysozyme and a sample N-acetyl-glucosamine bound to chicken egg lysozyme were prepared and analyzed. Lyophilized chicken egg lysozyme (E. C. 3.2.1.17; Fisher-Biotech, 3× crystallized, lot Nos. 995417-12 and 996924-12) and N-acetyl-glucosamine (NAG; ICN Biomedicals, Inc. lot No. R9745) 0.05 M $Na_2 HPO_4/KH_2 PO_4$ buffer pH 5.0 (Fisher Sci.), 0.05 M potassium hydrogen phthalate/NaOH buffer pH 5.0 (Hydrion, Aldrich Chemical Co.) and NaCl ("Certified for Biological Use", Fisher Sci.) were obtained and used as received. No diffraction peaks were seen when test powder diffraction measurements were taken on the lyophilized chicken lysozyme confirming that the raw unprocessed macromolecule, prior to the sample preparation steps, was unsuitable for use in the current invention.

A polycrystalline slurry of macromolecule-ligand was made by combining ~20 mg lysozyme (1.4 mmol), ~10 mg NAG (45 mmol) and 200 ml 0.5 M NaCl buffer pH 6.0 with an agate mortar and pestle. Polycrystalline precipitate formed within a few seconds. The slurry was loaded into a 1.5 mm diameter glass capillary and centrifuged to pack the slurry. Excess mother liquor was removed and the capillary was flame-sealed to prevent subsequent solvent evaporation.

The polycrystalline sample of unbound macromolecule lysozyme was prepared in a similar way in 0.5 M NaCl buffer pH 6.0 and under similar temperature and pressure conditions. Each of the samples was approximately 8 mm long within the capillary.

Shortly after each sample was prepared, high-resolution X-ray powder diffraction data were collected at room temperature (23° C.) on beamline X3b1 at the National Synchrotron Light Source, Brookhaven National Laboratory equipped with a double Si(111) monochromator and a Ge(111) analyzer; the sample was spun during data collection to ensure good powder averaging. Wavelength calibrations were obtained from the fitted positions of six reflections from an NIST SRM1976 alumina plate. Data were collected from approximately 2θ=0.5° to 14° in steps of approximately 0.002° with an X-ray wavelength of approximately 0.7 Å. Data-collection step count times were determined by the following algorithm: for 2θ<5°, t=4 s; for 2θ>5°, t=6.4691-0.9877(2θ)+0.0988(2θ)$^2$ s. See also Table 1 through Table 4.

The crystal structure of the unbound lysozyme was subject to a combined Rietveld and stereochemical restraint least-squares refinement using the General Structure Analysis System (GSAS). The starting model for the lysozyme atomic coordinates was taken from PDB entry 1rfp. Protein refinement was achieved by constructing a band-diagonal approximation to the full matrix; band-matrix routines from the SLATEC suite were adapted for use in GSAS. A matrix bandwidth of 300 parameters was chosen for refinement of all lysozyme structures studied here. During the Rietveld refinement the resulting protein stereochemistry was periodically evaluated with the PROCHECK suite of programs and graphically examined using the Swiss-PdbViewer package. The resulting fitted powder diffraction profiles are shown FIG. 6. The refined structure yielded the following residuals: $R_{wp}$=2.49%, $R_p$=1.95% and $R_F^2$=6.09%.

The lysozyme structure obtained was used as starting model for the analysis of the lysozyme-NAG powder diffraction data. A preliminary combined Rietveld and stereochemical refinement for the material, neglecting NAG from model yielded the following residuals: $R_{wp}$=2.61%, $R_p$=2.04%, $R_F^2$=6.03%. A difference Fourier map was constructed using structure factors extracted from the powder diffraction profile. The difference Fourier map prepared from these extracted intensities showed an extended region of density only in the vicinity of the previously identified C sugar-binding site for lysozyme. A model for the lysozyme-NAG complex was developed by placing a NAG molecule in the α-anomer form to best fit the extended density region observed in the difference Fourier map. After preliminary refinement of the position and orientation of the α-NAG molecule as a rigid body, the entire α-NAG-lysozyme complex was subjected to combined Rietveld and stereo-chemical refinement.

It can be seen that the location of the NAG interaction with the lysozyme active site was found from a difference Fourier map generated from structure factors extracted during a combined Rietveld and stereochemical refinement.

EXAMPLE 2

For comparison, studies of the interactions of $NAG_2$, $NAG_4$ and $NAG_5$ within the active sites of lysozyme were conducted. In this example, lyophilized chicken egg lysozyme (EC 3.2.1.17, FisherBiotech, 3× crystallized, lot Nos. 995417-12 and 996924-12) and N-acetylglucosamine oligomers (N,N'-diacetylchitobiose=$NAG_2$, $N_4$-tetraacetylchitotetrose=$NAG_4$, and $N_5$-pentaacetylchitopentose=$NAG_5$, Sigma-Aldrich), pH 6.0 0.05M $Na_2HPO_4$/$KH_2PO_4$ buffer (Fisher Sci.), and NaCl ("Certified for Biological Use", Fisher Sci.) were used as received.

In the sample preparations for lysozyme/$NAG_2$, and lysozyme/$NAG_4$ complexes, a polycrystalline slurry was made by combining 25 mg lysozyme (1.8 μmol), sufficient $NAG_n$ to be in slight excess of 1:1 stoichiometry with the lysozyme and 200 μl of 1.0M NaCl pH 6.0 buffer with an agate mortar and pestle. For lysozyme/$NAG_5$ 10 mg of protein was used. In each case a polycrystalline precipitate formed within a few seconds. The slurry was loaded into a 1.5 mm diameter glass capillary, and centrifuged to pack the slurry. Excess mother liquor was removed and the capillary flame sealed to prevent subsequent solvent evaporation. Samples were approximately 8 mm in length.

Shortly after sample preparation, X-ray powder diffraction data were collected at room temperature (23° C.) on beam line X3b1 at the National Synchrotron Light Source, Brookhaven National Laboratory, equipped with a double Si(111) monochromator and a Ge(111) analyzer set to a wavelength of 0.700 Å; the sample was spun during data collection to ensure good powder averaging. Wavelength calibrations were obtained from the fitted positions of six reflections from an NIST SRM1976 alumina plate. All scans covered the 2θ range 1.0-13° in 0.002° steps and were each collected over a 11-12 h period using the following algorithm for the step counting times: for 2θ<5° t=4s; for 2θ>5° t=6.4691-0.9877(2θ)+0.0988(2θ)$^2$s.

For each powder diffraction data set from the lysozyme/$NAG_2$, lysozyme/$NAG_4$ and lysozyme/$NAG_5$ complexes, respectively, an initial Rietveld refinement was performed adjusting only lattice parameters, scale factor, background parameters and line broadening parameters. The macromolecule model was taken from the Protein Data Base entry 1JA7 for a lysozyme/NAG complex with the NAG ligand removed. This model differs from the lysozyme/NAG example where the protein model was 1JA6, i.e. previously refined lysozyme from powder data.

Figure 7:
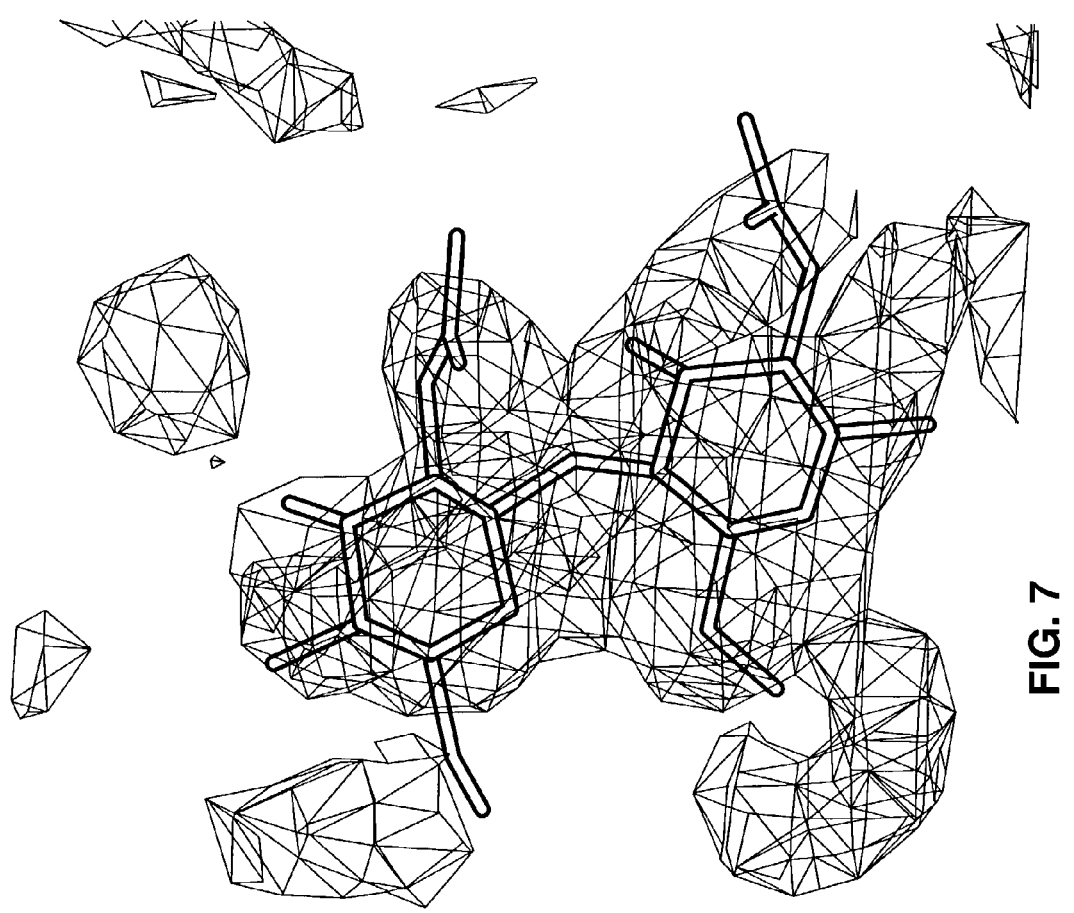
FIG. 7 is a difference Fourier map of the lysozyme-$NAG_2$ complex according to one aspect of the present invention.

A difference Fourier map was prepared in each case from a suite of structure factors extracted during the initial Rietveld refinements. Each map showed extended density features that matched in extent what would be expected from the molecular dimensions of the respective $NAG_n$ molecule only in the central binding groove of lysozyme. For example. FIG. 7 shows the density relative to the refined position of the $NAG_2$ molecule in the difference Fourier map. The appropriate $NAG_n$ molecule was fitted into place to best fit the difference map density using the molecular manipulation tools available in SPDBV. Complete combined Rietveld and stereochemical restraint refinements were then employed. The resulting structures were checked for protein reasonableness with the PROCHECK suite and examined with the energy calculations (GROMOS based) available in SPDBV. The occupancy of each $NAG_n$ was checked by allowing the atom site fractions to vary as a unit for each NAG group; site occupancies in excess of 90% were found when correct placement of each NAG group was attained. Incorrectly placed or oriented NAG groups showed substantially lower site occupancies.

For lysozyme/$NAG_4$ and lysozyme/$NAG_5$, the site occupancy refinements revealed that at the beginning of the analysis portions of the $NAG_n$ molecule were incorrectly placed; improvement was attained by use of OMIT maps. These were produced by the following steps: 1) set atom site fractions to zero for group in question 2) extract new structure factors from powder pattern via Rietveld method 3) generate difference Fourier map 4) examine density for proper placement of group 5) perform combined Rietveld and stereochemical restraint refinement with new structure. Bad non-bonded contacts were detected by either PROCHECK or energy calculations (GROMOS) in SPDBV; these were fixed by minor manipulations of the $NAG_n$ and/or lysozyme amino acid side chains as needed. A final combined Rietveld and stereochemical restraint refinement was used to complete the structure analysis in each case.

Figure 8:
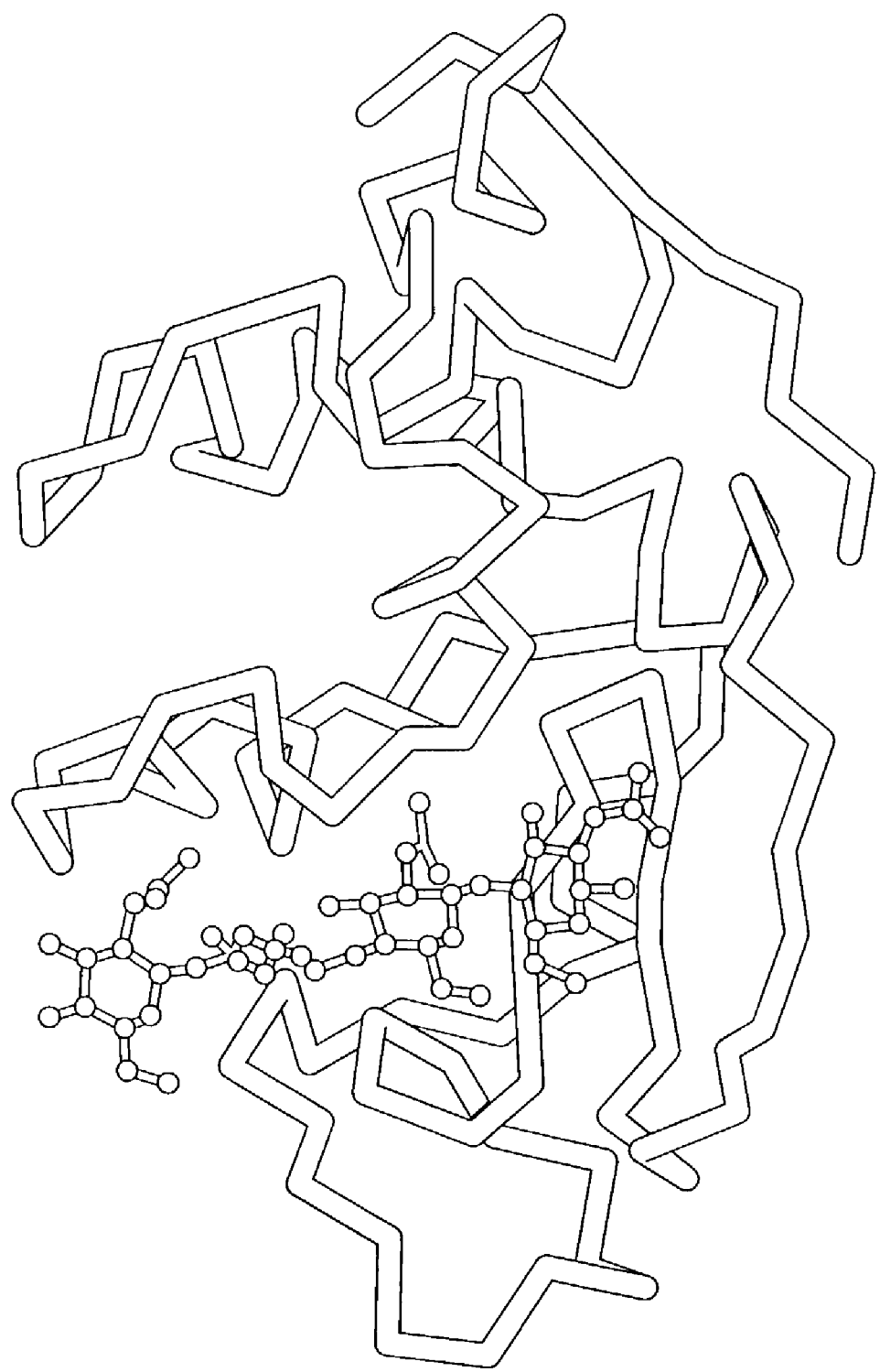
FIG. 8 is the derived molecular structure of lysozyme-$NAG_4$ complex according to one aspect of the present invention.

Details of the data collections are given in Table 4 and Table 5. The derived structure of the lysozyme/NAG$_4$ complex is shown in FIG. 8.

EXAMPLE 3

A sample of lyophilized chicken egg lysozyme was prepared and analyzed using neutrons as a diffraction source. Lyophilized chicken egg lysozyme (E.C. 3.2.1.17; FisherBiotech, 3× crystallized, lot Nos. 995417-12 and 996924-12) and 1.0 M NaCl, pH 4.0 buffer prepared in D$_2$O and combined in an agate mortar and pestle. D$_2$O is used to avoid some of the very high incoherent scattering from hydrogen that is typically observed.

The resulting slurry was placed in a quartz NMR tube approximately 5 mm in diameter and approximately 50 mm in length. The sample was placed in the "High Intensity Powder Diffractometer" (HIPD) with 14° detectors at the Los Alamos National Science Center for a 12 hour run. The source strength was 100 µA. The unit cell was tetragonal, P4$_3$ 2$_1$ 2 with a=78.72 Å, c=38.26 Å and Z=8

Figure 9:
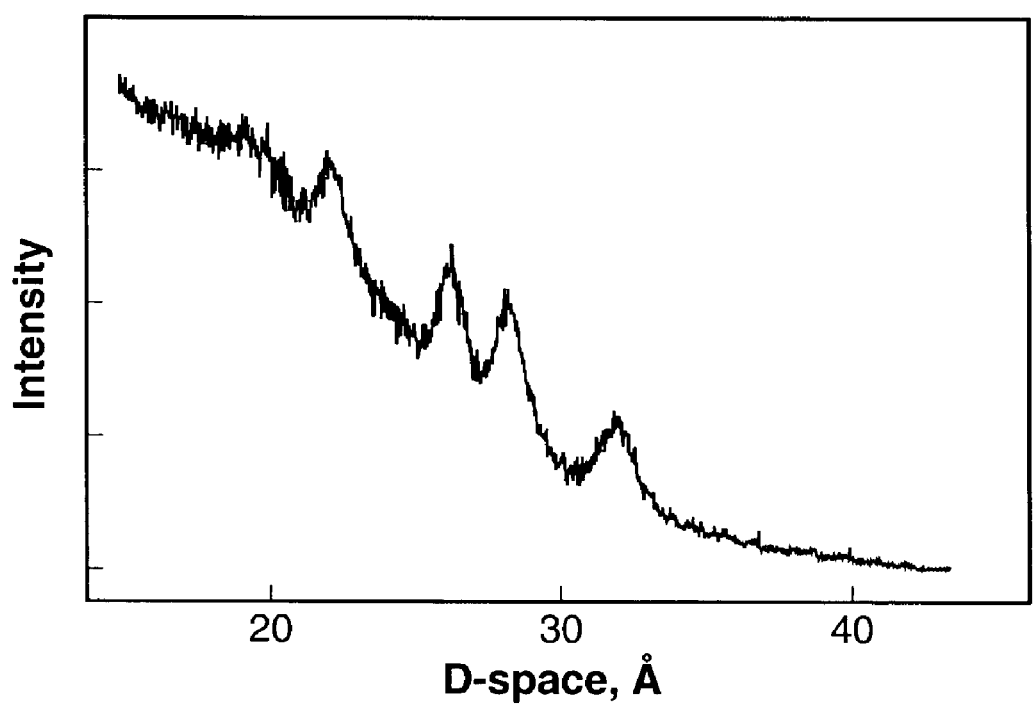
FIG. 9 is a graph of neutron powder diffraction from unbound lysozyme according to one aspect of the present invention.

The results seen in FIG. 9, suggest that d-spacings as small as 5 Å could be seen given this intensity with longer run times. This is believed to be the first and only neutron protein powder diffraction pattern to date where peaks are definitely seen. New higher intensity instruments envisioned for the next generation neutron sources will likely attain improved resolution and shorter data collection times. From the foregoing description and examples, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed herein, they are intended in a descriptive sense and not for purposes of limitation.

Accordingly, it will be seen that the methods of this invention can be applied to any number of macromolecule-ligand complexes including nucleic acid-protein complexes, protein-protein and multiple protein-ligand complexes. The disclosed methods permit the identification of new active sites on the macromolecule as well as the interactive sites on the ligand.

It will also be seen that this invention provides a method of crystallizing material that is particularly suited for producing microcrystalline powders of macromolecules and macromolecule-ligand complexes for analysis by powder diffraction techniques.

Although the description above contains many specificities, this should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1

Crystallographic Data for N-acetyl-D-glucosamine/lysozyme Complex Crystal Data

| Material | Lysozyme | NAG/Lysozyme |
| --- | --- | --- |
| Space group | P4$_3$2$_1$2 | P4$_3$2$_1$2 |
| a (Å) | 79.1317(11) | 78.9631(10) |
| c (Å) | 38.0297(10) | 38.2151(10) |
| V (Å$^3$) | 238135(8) | 238277(9) |

TABLE 2

Crystallographic Data for N-acetyl-D-glucosamine/lysozyme Complex Powder Data Collection

| Material | Lysozyme | NAG/Lysozyme |
| --- | --- | --- |
| Buffer pH | 6.00 | 6.00 |
| Measured pH | 5.2 | 5.1 |
| λ (Å) | 0.699970(1) | 0.699842(1) |
| 2θ range (°) | 1.0-13.580 | 1.0-13.498 |
| Δ2θ (°) | 0.002 | 0.002 |
| Steps | 6291 | 6250 |
| Step time (s) | 4.0-11.25 | 4.0-11.13 |

TABLE 3

Crystallographic Data for N-acetyl-D-glucosamine/lysozyme Complex Combined Rietveld and Stereochemical Restraint Refinement

| Material | Lysozyme | NAG/Lysozyme |
| --- | --- | --- |
| N$_{ref}$ | 2824 | 2758 |
| Resolution (Å) | 40.11-2.96 | 40.10-2.98 |
| N$_{restrains}$ | 5019 | 5091 |
| N$_{obs}$ | 11310 | 11341 |
| N$_{parameters}$ | 3025 | 3069 |
| R$_{wp}$ | 2.49% | 2.48% |
| R$_{p}$ | 1.95% | 1.94% |
| R$_F^2$ | 6.09% | 4.95% |

TABLE 4

Crystallographic data for NAG$_2$, NAG$_4$ and NAG$_5$/lysozyme Complexes Powder Data Collection

| Material | NAG$_2$/Lysozyme | NAG$_4$/Lysozyme | NAG$_5$/Lysozyme |
| --- | --- | --- | --- |
| Buffer pH | 6.00 | 6.00 | 6.00 |
| λ (Å) | 0.7 | 0.7 | 0.7 |
| 2θ range (°) | 1.000-13.604 | 1.000-12.498 | 1.000-12.498 |
| Δ2θ (°) | 0.002 | 0.002 | 0.002 |
| Steps | 6253 | 5750 | 5750 |

TABLE 5

Crystallographic data for $NAG_2$, $NAG_4$ and $NAG_5$/lysozyme Complexes
Combined Rietveld and Stereochemical Restraint Refinement

| Material | $NAG_2$/Lysozyme | $NAG_4$/Lysozyme | $NAG_5$/Lysozyme |
|---|---|---|---|
| Resolution (Å) | 40.13-2.98 | 40.13-3.22 | 40.13-3.22 |
| $N_{restraints}$ | 6110 | 6282 | 6340 |
| $N_{parameters}$ | 3112 | 3195 | 3237 |
| $R_{wp}$ | 2.40% | 2.42% | 2.41% |
| $R_p$ | 1.88% | 1.90% | 1.86% |
| $R_F^2$ | 3.99% | 4.71% | 4.96% |
| NAG Ring Occupancy | 95+% | 95+% | 90+% |

What is claimed is:

1. A method for determining the structure of a macromolecule-ligand complex, comprising:
   (a) producing a sample of a selected polycrystalline macromolecule-ligand complex, said sample produced by the steps comprising
      (i) providing a quantity of substantially dehydrated macromolecules and a quantity of ligand molecules, and
      (ii) adding a liquid to a mixture of said dehydrated macromolecules and said ligand molecules while physically agitating the mixture of said macromolecules and said ligand molecules, wherein said polycrystallites of said macromolecule-ligand complex are formed;
   (b) producing a sample of a selected polycrystalline macromolecule, said sample produced by the steps comprising
      (i) providing a quantity of substantially dehydrated macromolecules, and
      (ii) adding a liquid to said dehydrated macromolecules while physically agitating said macromolecules, wherein said polycrystallites of said macromolecule are formed;
   (c) providing a molecular model of the selected macromolecule;
   (d) collecting powder diffraction data from said sample of said macromolecule and said sample of macromolecule-ligand complex; and
   (e) analyzing said diffraction data and said molecular model to yield the structure of said macromolecule-ligand complex.

2. A method as recited in claim 1, further comprising:
   determining the interaction of said ligand with said macromolecule; and
   comparing the interaction of said ligand with said macromolecule with the interaction of a different ligand with said macromolecule.

3. A method as recited in claim 1, wherein said dehydrated macromolecules have been lyophilized.

4. A method as recited in claim 1, wherein said ligand molecules have been lyophilized.

* * * * *